US012057211B2

(12) United States Patent
Sandritter et al.

(10) Patent No.: US 12,057,211 B2
(45) Date of Patent: Aug. 6, 2024

(54) PREDICTING AN ADVERSE PHYSICAL EFFECT BASED ON TIME SERIES DATA

(71) Applicant: Rippleworx, Inc., Huntsville, AL (US)

(72) Inventors: Angela Michelle Sandritter, Huntsville, AL (US); Timo Sandritter, Huntsville, AL (US); Mark Harold Howard, II, Canton, GA (US); Jason P. DeVine, Alpharetta, GA (US)

(73) Assignee: Rippleworx, Inc., Huntsville, AL (US)

( * ) Notice: Subject to any disclaimer, the term of this patent is extended or adjusted under 35 U.S.C. 154(b) by 433 days.

(21) Appl. No.: 17/140,418

(22) Filed: Jan. 4, 2021

(65) Prior Publication Data

US 2021/0210187 A1 Jul. 8, 2021

Related U.S. Application Data

(60) Provisional application No. 62/957,498, filed on Jan. 6, 2020.

(51) Int. Cl.
*G16H 20/30* (2018.01)
*G16H 40/63* (2018.01)

(52) U.S. Cl.
CPC ............ *G16H 20/30* (2018.01); *G16H 40/63* (2018.01)

(58) Field of Classification Search
None
See application file for complete search history.

(56) References Cited

U.S. PATENT DOCUMENTS

2004/0209600 A1* 10/2004 Werner ................. H01Q 1/273
455/414.1
2007/0219059 A1* 9/2007 Schwartz ........... A61B 5/02405
482/8
2016/0263440 A1* 9/2016 Martin ............... A63B 24/0062
2020/0360765 A1* 11/2020 Higuchi ................. A61B 5/222

FOREIGN PATENT DOCUMENTS

CN 112755458 A * 5/2021 ......... A63B 22/0605

OTHER PUBLICATIONS

Alaunyte, Ieva, et al. "Dietary Iron Intervention using a Staple Food Product for Improvement of Iron Status in Female Runners." Journal of the International Society of Sports Nutrition 11 (2014). (Year: 2014).*
Ishida, Ai. "The Ability of Internal and External Workload to Predict Soft Tissue Injury of the Lower Limbs in College Female Soccer Players." Order No. 10811344 Arizona State University, 2018. Ann Arbor: ProQuest. Web. Sep. 5, 2023. (Year: 2018).*

* cited by examiner

*Primary Examiner* — Lena Najarian
(74) *Attorney, Agent, or Firm* — Kilpatrick Townsend & Stockton LLP

(57) ABSTRACT

Systems and methods manage goals and tasks for individuals based on factors such as time-series data retrieved from a wearable device, user input to one or more computing devices, and analysis of data corresponding to other individuals. Time series data retrieved from a wearable device is used to compute a value that is used to predict a warning of an adverse physical effect for an individual. Data such as heartrate, blood oxygenation, and/or distance traveled for an athlete, along with a recorded indication of the athlete's physical exertion for an athletic session, is used to compute a value that indicates whether an adverse physical effect is likely. If the value exceeds a threshold, then the system transmits a warning and/or modifies the individual's schedule for display on a calendar.

10 Claims, 19 Drawing Sheets

400

```
┌─────────────────────────────────────────────────────────────────────┐
│  RECEIVE A FIRST DATA SET COMPRISING FIRST TIMESTAMPS, AN IDENTIFIER OF │
│           AN INDIVIDUAL, AND A PLURALITY OF FIRST MEASUREMENTS      │
│                                 402                                 │
└─────────────────────────────────────────────────────────────────────┘
                                   │
                                   ▼
┌─────────────────────────────────────────────────────────────────────┐
│         RECEIVE A SECOND DATA SET COMPRISING A PLURALITY OF SECOND  │
│       TIMESTAMPS, THE IDENTIFIER OF THE INDIVIDUAL, AND A PLURALITY OF │
│                          SECOND MEASUREMENTS                        │
│                                 404                                 │
└─────────────────────────────────────────────────────────────────────┘
                                   │
                                   ▼
┌─────────────────────────────────────────────────────────────────────┐
│  CORRELATE THE FIRST DATA SET AND THE SECOND DATA SET BASED ON THE  │
│  IDENTIFIER OF THE INDIVIDUAL, THE PLURALITY OF FIRST TIMESTAMPS, AND │
│                 THE PLURALITY OF SECOND TIMESTAMPS                  │
│                                 406                                 │
└─────────────────────────────────────────────────────────────────────┘
                                   │
                                   ▼
┌─────────────────────────────────────────────────────────────────────┐
│    BASED ON THE CORRELATED FIRST DATA SET AND SECOND DATA SET, PREDICT │
│                       AN ADVERSE PHYSICAL EFFECT                    │
│                                 408                                 │
└─────────────────────────────────────────────────────────────────────┘
                                   │
                                   ▼
┌─────────────────────────────────────────────────────────────────────┐
│           TRANSMIT A WARNING OF THE ADVERSE PHYSICAL EFFECT         │
│                                 410                                 │
└─────────────────────────────────────────────────────────────────────┘
```

FIG. 4

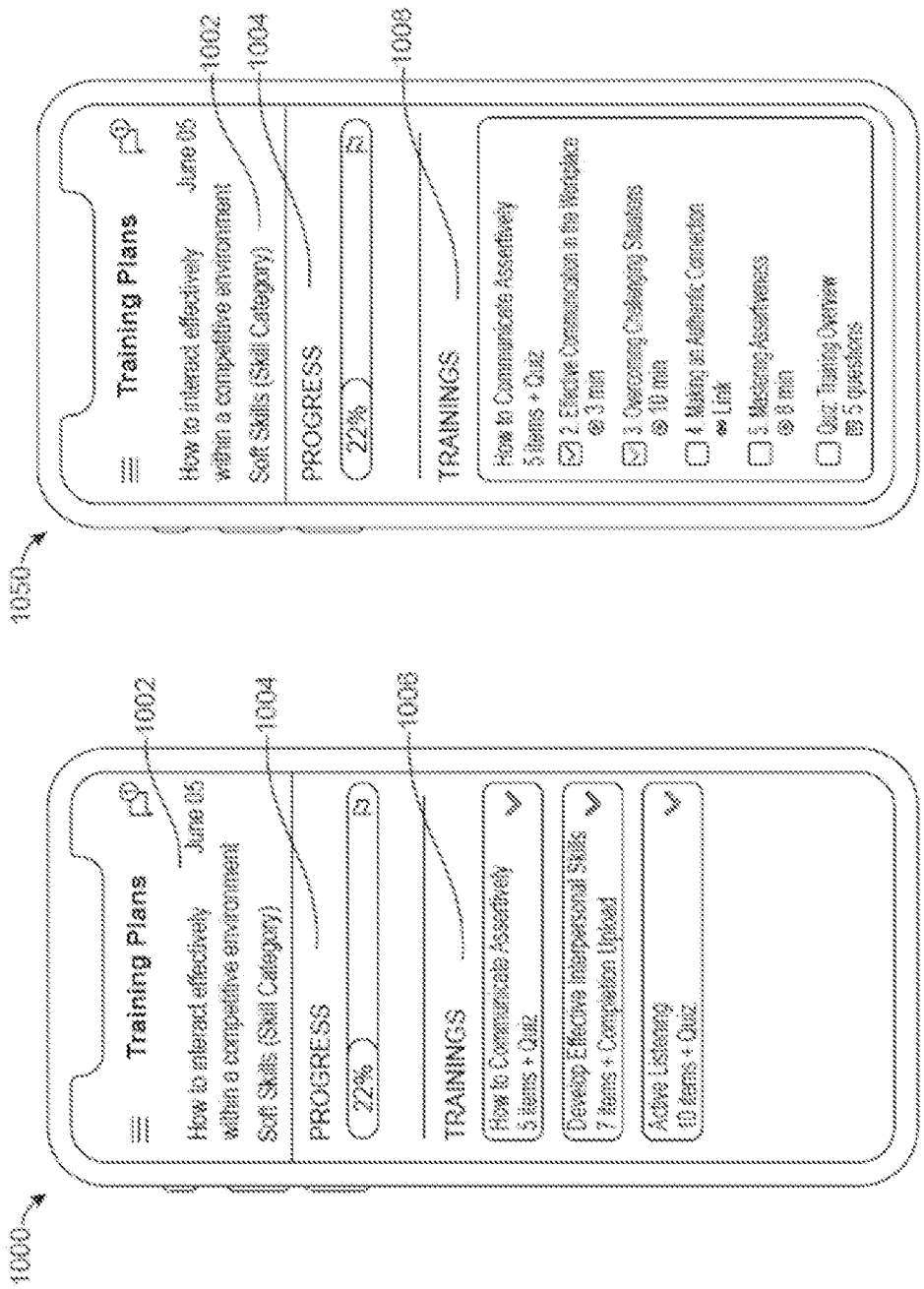

PREDICTING AN ADVERSE PHYSICAL EFFECT BASED ON TIME SERIES DATA

CROSS-REFERENCES TO RELATED APPLICATIONS

This application claims the benefit of priority under 35 U.S.C. § 119 from U.S. Provisional Application No. 62/957,498, filed on Jan. 6, 2020, the disclosure of which is hereby incorporated by reference in its entirety for all purposes.

BACKGROUND

It is increasingly popular to receive and analyze user data related to physical condition. For example, user devices that monitor physical states like steps taken and heart rate are widely used. Wearable devices may gather biometric information and perform simple computations based on the gathered biometric information. For example, wearable devices may compute an average number of steps taken per day, or convert a pulse rate to a heart rate. The biometric data gathered by these devices is increasingly valuable as new methods are developed for gathering, analyzing, and using the data.

BRIEF SUMMARY

Systems and methods are described for predicting an adverse physical effect based on time series data. Data associated with one or more users is retrieved. Biometric data may be gathered from a wearable device. User feedback may also be gathered from a user interface of a user device. The system may correlate multiple types of data over time to identify patterns indicating a likelihood of adverse physical effect, such as an injury. The system may output a warning upon determining that the adverse physical effect is likely. The system may also cause display of a user interface allowing a user to drill down into different data sets for different individuals. In some aspects, goals are managed for individuals within an organization using a skills matrix to determine and display progress towards one or more goals for an individual baselined as a function of other individuals in the organization.

In some embodiments, a method of forecasting and preventing a non-contact injury of an athlete includes receiving an average heartrate, average blood oxygenation, or distance traveled of an athlete for an athletic session, receiving a recorded subjective perception from the athlete of the athlete's physical exertion for the athletic session, the subjective perception recorded after the athletic session, multiplying the average heartrate, the average blood oxygenation, or the distance traveled by the subjective perception in order to produce a work load for the session, computing a ratio of the work load to an average of workloads over multiple weeks of sessions, and transmitting a warning that is triggered based on the ratio breaching a threshold value, the warning indicating a predicted adverse physical effect.

In some aspects, the method further includes modifying a calendar of the athlete to remove a training session or replace a first type of training session with a second type of training session. In some aspects, the method further includes determining a position or role of the athlete, searching a training matrix based on the position or role of the athlete, accessing the calendar for the athlete, and comparing at least one training session in the calendar to recommendations in the training matrix, wherein the modifying of the calendar is based on the comparison.

In some aspects, transmitting the warning includes sending a first electronic mail (email) message. In some aspects, the method further comprises including in the first email message the average heartrate, the average blood oxygenation, or the distance traveled, the first email being sent to the athlete and preparing a second email message, the second email message identifying the athlete but omitting the average heartrate, the average blood oxygenation, or the distance traveled, the second email being sent to a coach of the athlete.

In some aspects, the threshold value for the ratio is 1.5. In some aspects, the method further includes receiving timestamped heartrate data or timestamped blood oxygenation data and averaging the timestamped heartrate data or timestamped blood oxygenation data in order to calculate the average heartrate or the average blood oxygenation.

In some embodiments, a system includes a processor and a non-transitory computer readable medium operatively coupled to the processor, the non-transitory computer readable medium comprising code executable by the processor for performing a method comprising: receiving a first data set comprising a plurality of first timestamps, an identifier of an individual, and a plurality of first measurements, receiving a second data set comprising a plurality of second timestamps, the identifier of the individual, and a plurality of second measurements, correlating the first data set and the second data set based on the identifier of the individual, the plurality of first timestamps, and the plurality of second timestamps, based on the correlated first data set and second data set, predicting an adverse physical effect, and transmitting a warning of the adverse physical effect.

In some aspects, the method performed by the system further comprises modifying a calendar of the individual to remove an activity or replace a first type of activity with a second type of activity. In some aspects, the system further comprises a heart rate monitor and one of a Global Positioning System (GPS) or oximetry sensor, the first measurements are heartrate measurements, and the second measurements are one of: distance measurements, acute chronic work load ratio measurements, or blood oxygenation measurements.

In some aspects, the first measurements are blood oxygenation measurements and the second measurements relate to a status of a vehicle. In some aspects, the predicting the adverse physical effect comprises using a predictive model trained on historical data to determine that a computed value exceeds a threshold value. In some aspects, the adverse physical effect is an injury or asphyxia. In some aspects, the method performed by the system further comprises causing display of a graphical user interface including a graph of the plurality of first measurements and the plurality of second measurements over a time period.

In some embodiments, a computer-implemented method comprises identifying a goal for an individual in an organization, determining a current skill level for the individual associated with the goal, determining a target skill level for meeting the identified goal, based on skill levels of other individuals in the organization, based on comparing the current skill level to the target skill level, modifying a schedule for the individual to add, remove, or change a scheduled activity, and causing display of a calendar on a graphical user interface, the calendar comprising the modified schedule.

In some aspects, the method further comprises determining a second current skill level for the individual for a second skill associated with the goal, determining a second target skill level for a second skill for meeting the identified goal, based on the skill levels of the other individuals in the organization, and, based on comparing the current skill level to the target skill level for the second skill, further modifying the schedule for the individual.

In some aspects, the graphical user interface is a first graphical user interface and the skill is a first skill, and the first skill and the second skill for meeting the identified goal are configured via input to a second graphical user interface. In some aspects, the method further comprises receiving a data set comprising a plurality of timestamps, an identifier of the individual, and a plurality of measurements associated with the individual, wherein the current skill level for the individual is computed based on the data set.

In some aspects, the measurements comprise heartrate measurements, distance measurements, acute chronic work load ratio measurements, blood oxygenation measurements, speeds of completing a task, or activities completed. In some aspects, the method further comprises, based on the data set for the individual, predicting an adverse effect, wherein modifying the schedule comprises removing or changing the scheduled activity responsive to predicting the adverse effect.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

FIG. 4 is a flow chart illustrating additional techniques for predicting an adverse physical effect according to some embodiments.

FIG. 10A illustrates an example user interface illustrating training plan progress, according to some embodiments.

FIG. 10B illustrates another example user interface illustrating training plan progress, according to some embodiments.

DETAILED DESCRIPTION

Embodiments include techniques for managing goals and tasks for individuals, which may be executed based on factors such as time-series data retrieved from a wearable device, user input to one or more computing devices, and analysis of data corresponding to other individuals. In some aspects, time series data retrieved from a wearable device is used to compute a value that is used to predict a warning of an adverse physical effect for an individual. For example, heartrate, blood oxygenation, and/or distance traveled for an athlete, along with a recorded indication of the athlete's physical exertion for an athletic session, is used to compute a value that indicates whether an adverse physical effect such as a non-contact injury is likely. This may be performed by correlating two data sets based on an identifier of the individual and a plurality of timestamps in each data set. If the value exceeds a threshold, then the system may transmit a warning and/or modify the individual's schedule for display on a calendar. Alternatively, or additionally, the skill level for the individual may be assessed by the system in comparison to a set of goals for a particular role in an organization. The system uses a skills matrix to manage actions and progress for an individual to accomplish various skills. This skills matrix can be modified responsive to factors such as predicting an adverse physical effect, determining an individual's progress in one or more skills, and receiving user-configured modifications to the goals and skills.

Figure 1:
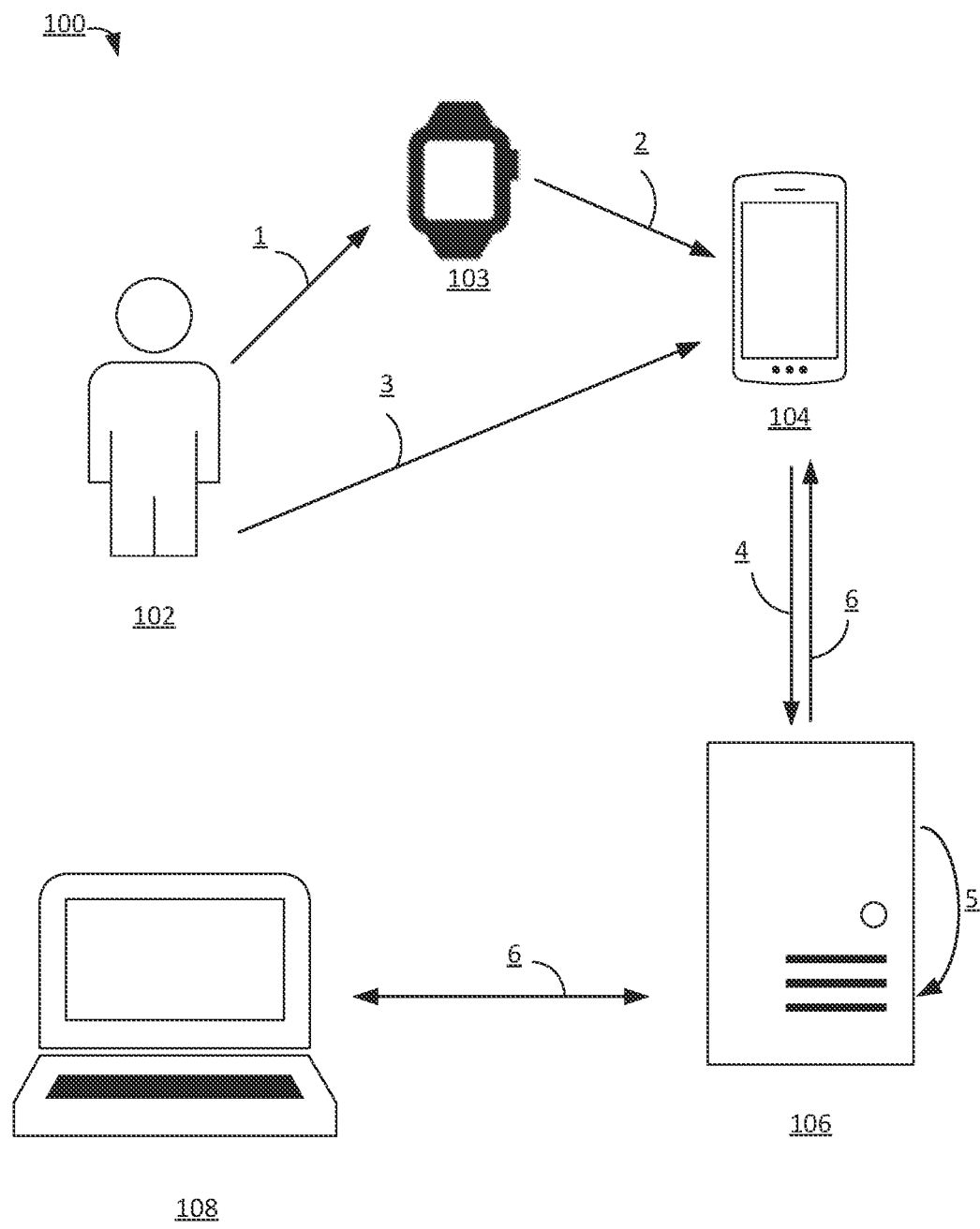
FIG. 1 illustrates a schematic diagram of a system and method for predicting an adverse physical effect based on time series data according to some embodiments.

FIG. 1 illustrates a schematic diagram 100 of a system and method for predicting an adverse physical effect based on time series data according to some embodiments. The system may include a user 102, a first user device 104, a wearable device 103, a server computer 106, and a second user device 108. For simplicity of illustration, a limited number of components are shown in FIG. 1. It is understood, however, that embodiments may include more than one of each component.

In some embodiments, the system and method depicted in FIG. 1 provide an injury prevention solution that combines daily physical monitoring, daily human output measurement, and configurable alerting in order to provide an advanced warning for mitigating injury risk.

The components in the system depicted in FIG. 1 can be in operative communication with each other through any suitable communication channel or communications network. Suitable communications networks may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. Messages between the computers, networks, and devices may be transmitted using a secure communications protocols such as, but not limited to, File Transfer Protocol (FTP); HyperText Transfer Protocol (HTTP); Secure Hypertext Transfer Protocol (HTTPS); Secure Socket Layer (SSL), and/or the like.

In some embodiments, the user 102 is an individual being monitored by the system. The user 102 may, for example, be an athlete, a pilot, or an employee. The user 102 interacts with the wearable device 103 and first user device 104, which gather information about the user 102.

The wearable device 103 is a device wearable by a user (e.g., user 102) and capable of obtaining data about the user 102. The wearable device 103 may, for example, be a vest, watch, ring, hat, or the like. The wearable device 103 may include hardware for detecting the data about the user 102 such as a heart rate monitor, an oximetry sensor, a blood pressure detector, a Global Positioning System (GPS), and so forth. The data about the user 102 may include biometric information such as heartrate information, pulse information, blood oxygen levels, and blood salinization levels. The data about the user 102 may include location information (e.g., location data detected using GPS functionality).

The first user device 104 is a device operable by a user (e.g., user 102) and capable of executing applications. As examples, the first user device 104 may be a smartphone, a computer, a tablet, or the like. The first user device 104 may also include hardware and/or software configured to store data. The first user device 104 may also include hardware and/or software configured to receive data from the wearable device 103. The first user device 104 may include hardware and/or software configured to transmit data to the server computer 106. The first user device 104 may also be connected to the server computer 106 via a communication network. The first user device 104 may also include hardware and/or software capable of receiving user input. The first user device 104 may also include a keyboard, touchscreen, microphone, and/or the like for receiving data from a user. The first user device 104 may also receive information about the user 102, via direct user input (e.g., the user inputs an answer to a question via a user interface displayed by the first user device 104) and/or by way of the wearable device 103 (e.g., via a wireless connection and a coupled application).

The server computer 106 may include functionality to receive and analyze data received from the first user device 104 and/or the wearable device 103. The server computer 106 may include a processor coupled to a memory, a network interface, and a computer-readable medium, as described in further detail below with respect to FIG. 2. In some embodiments, the server computer 106 is configured to gather data from the first user device 104 and/or wearable device 103, and analyze this data to predict an adverse physical effect and/or manage a plan for the user 102.

The second user device 108 is a device operable by a user and capable of executing applications. In some embodiments, the user operating the second user device is different than the user 102 operating the first user device 104. For example, the second user device 108 may be operated by someone in a supervisory role with respect to the user 102 of the first user device 104. As a specific example, user 102 is an athlete, and the second user device 108 is operated by a coach that supervises user 102 along with other athletes on a team. As another example, user 102 is a pilot or soldier, and the second user device 108 is operated by a commander that supervises user 102 along with other pilots or soldiers in a division. The second user device 108 may otherwise be similar to the first user device 104.

In some embodiments, at step 1, the wearable device 103 collects data related to user 102. For example, the wearable device 103 may detect a pulse of the user, which may be converted to heartrate information. As another example, the wearable device 103 may detect the user's blood oxygenation and/or blood salinity levels. As another example, the wearable device 103 may detect location information associated with the user (e.g., the user's GPS coordinates). The wearable device 103 may record a timestamp with each element of user data. For example, the wearable device 103 collects a set of coordinates with respective timestamps at which the coordinates were retrieved. In some embodiments, at step 2, the wearable device 103 transmits the user data to the first user device 104 which may, in turn, transmit the user data to the server computer 106. Alternatively, or additionally, the wearable device 103 may transmit the user data directly to the server computer 106. The wearable device 103 and/or the first user device 104 may analyze the user data. For example, the wearable device 103 may compute a heart rate based on a detected pulse. As another example, the first user device 104 may compute a distance traveled and/or speed based on a set of GPS coordinates collected over time. In some embodiments, aggregate statistics, such as an average, minimum, maximum, event count, etc., is computed from time series data on-board the wearable device or the first user device.

In some embodiments, at step 3, the user 102 inputs data to the first user device 104. The user 102 may interact with the first user device 104 via interfaces (e.g., as illustrated in FIGS. 5A-5D). The user may input subjective perceptions of the user's physical state. For example, the user may input information about how well rested the user feels, how tired the user feels after an activity such as a workout or flying a plane, what the user has eaten that day, and so forth. As an example, the user may be an athlete, and the user may input a numerical value representing a subjective perception of the user's physical exertion for an athletic session. The athlete may input, and the system may record, the subjective perception after the athletic session.

At step 4, the first user device 104 (and/or the wearable device 103) may transmit information to the server computer 106. The server computer 106 may receive the information from the first user device 104 and/or the wearable device 103. The information may be time series data, i.e., a set of data with corresponding time stamps that can be used to analyze patterns in the data over time. In some embodiments, the first user device 104 transmits a first data set and second data set—e.g., two sets of time series data for different measurements. As an example, a first data set may be from the wearable device 103, e.g., heartrate, pulse, oximetry, and so forth. A second data may be from the first user device 104, e.g., information input by the user. Alternatively, or additionally, multiple data sets may be received from the wearable device 103 and/or the first user device 104. For example, heartrate and oximetry information may be received from the first user device 104 originating from the wearable device 103.

In some embodiments, information may be received from another source. As an example, the server computer 106 may receive user information from a computer operated by a doctor administrating tests to the user 102. As another example, the server computer 106 may receive information from a vehicle operated by the user 102. The information may relate to a status of the vehicle. For example, the user 102 may operate an airplane, and the airplane may transmit altitude information, speed information, GPS information, and so forth, to the server computer 106. As other examples, a vehicle (e.g., a car, truck, tank, or submarine operated by the user) may transmit vehicle information to the server computer 106. As another example, the server computer 106 may receive player statistics (e.g., passing accuracy, shooting percentage, and so forth) from a third-party service. As another example, the server computer may receive test scores or training confirmations from another computing device.

At step 5, the server computer 106 analyzes the received data. The server computer 106 may perform statistical operations on the received data such as sum, count, average, and standard deviation. The server computer 106 may correlate the first data set and the second data set based on timestamps. For example, the server computer may correlate a heart rate and an oximetry level based on same or similar timestamps (e.g., within one second or ten seconds of one another). The data points in the first data set and the second data set may be correlated over time to analyze how the first data set and the second data set relate to one another (e.g., time series data).

Figure 5B:
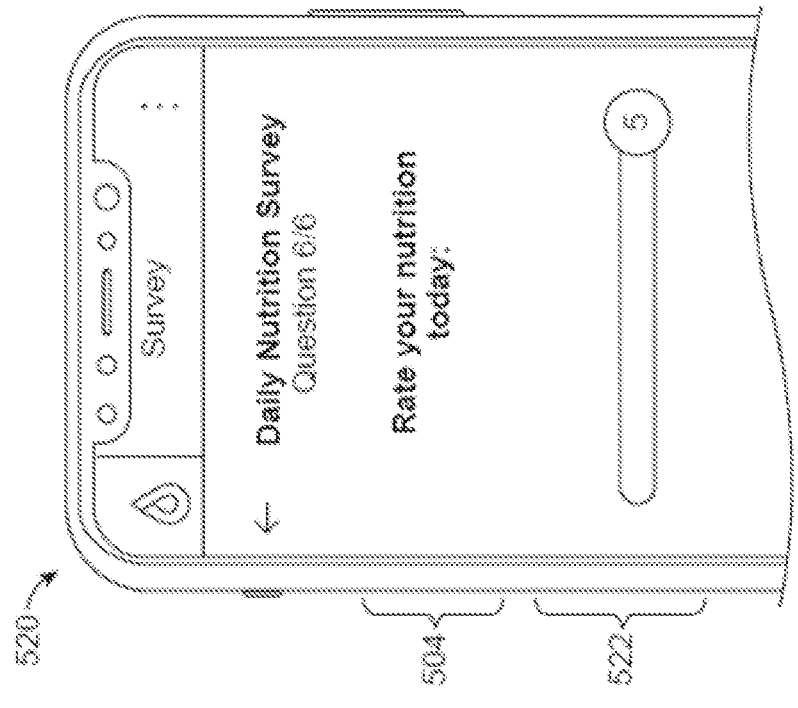
FIG. 5B illustrates an example user interface for receiving user information according to some embodiments.

As an example, the server computer 106 may determine an acute chronic work load ratio (ACWR) for a user. The acute chronic work load ratio is the ratio of an acute work load (work load over a relatively short time period) to a chronic work load (work load over a longer time period). For example, the system takes user feedback specifying how strenuous a user would rate a daily session and multiplies it by distance travelled for this daily session to compute a daily "work load". This mathematical operation, in effect, serves to normalize the subjective response to the survey question above. We call the output of this calculation the "work load" or "acute work load." After the data for each session is loaded into the system, the server computer automatically calculates the ratio of the current session work load to the player's chronic workload. This ratio is called the "Acute Chronic Work load Ratio" (ACWR). The ratio of the acute to chronic work load represents how exerted the user believes he is compared to a baseline. As another example, the acute work load is a user's perceived exertion (which may be received via user input to an interface as shown in FIGS. 5B and 5C) multiplied by a workout duration (e.g., 90 minutes, which may be determined based on user input and/or data detected by a wearable device), averaged over a one-week period. The chronic workload may be computed as an average of workloads over multiple weeks of sessions (e.g., 28 days).

In some embodiments, the server computer 106 generates a visualization of the time series data and cause display of the time series data. (Example visualizations are shown in FIGS. 7A-7E.)

In some embodiments, the server computer 106 predicts an adverse physical effect based on the correlated first data set and second data set. The prediction may be performed based on historical data, e.g., using a predictive model trained on historical data, such as prior data sets. The predictive model may, for example, be a machine-learning model.

As a specific example, the server computer 106 may analyze prior data sets (potentially for multiple users) to determine that, if a linear combination of a user's heartrate and the user's acute chronic work load ratio exceeds a threshold value, then an injury to the user is likely (e.g., within the coming day or week). As another example, the server computer 106 may analyze prior data sets to determine that, if a user's blood oxygen has dipped by 20% while a plane's altitude has changed by 40% or more, asphyxia is likely within the next several minutes. In some cases, the predicted adverse effect may be associated with a particular time period.

In some embodiments, the server computer 106 may compute a value (e.g., the ACWR), and compare the value to a predetermined threshold value, to determine whether an adverse physical effect is likely. For example, the system may allow a user to tune a threshold value (e.g., 1.5 for the ACWR), above which an adverse physical effect is deemed likely.

At step 6, the server computer 106 transmits a warning of the adverse physical effect. The warning may be transmitted to the second user device 108 and/or the first user device 104. The warning may be in the form of a push notification, and email, a text message, and/or the like. Alternatively, or additionally, the server computer 106 may cause display of an indication of the adverse physical effect via a user interface. As illustrated in FIGS. 7A-7E, color codes may be used to indicate an adverse physical effect has occurred, is likely to occur, or is not likely to occur.

Figure 2:
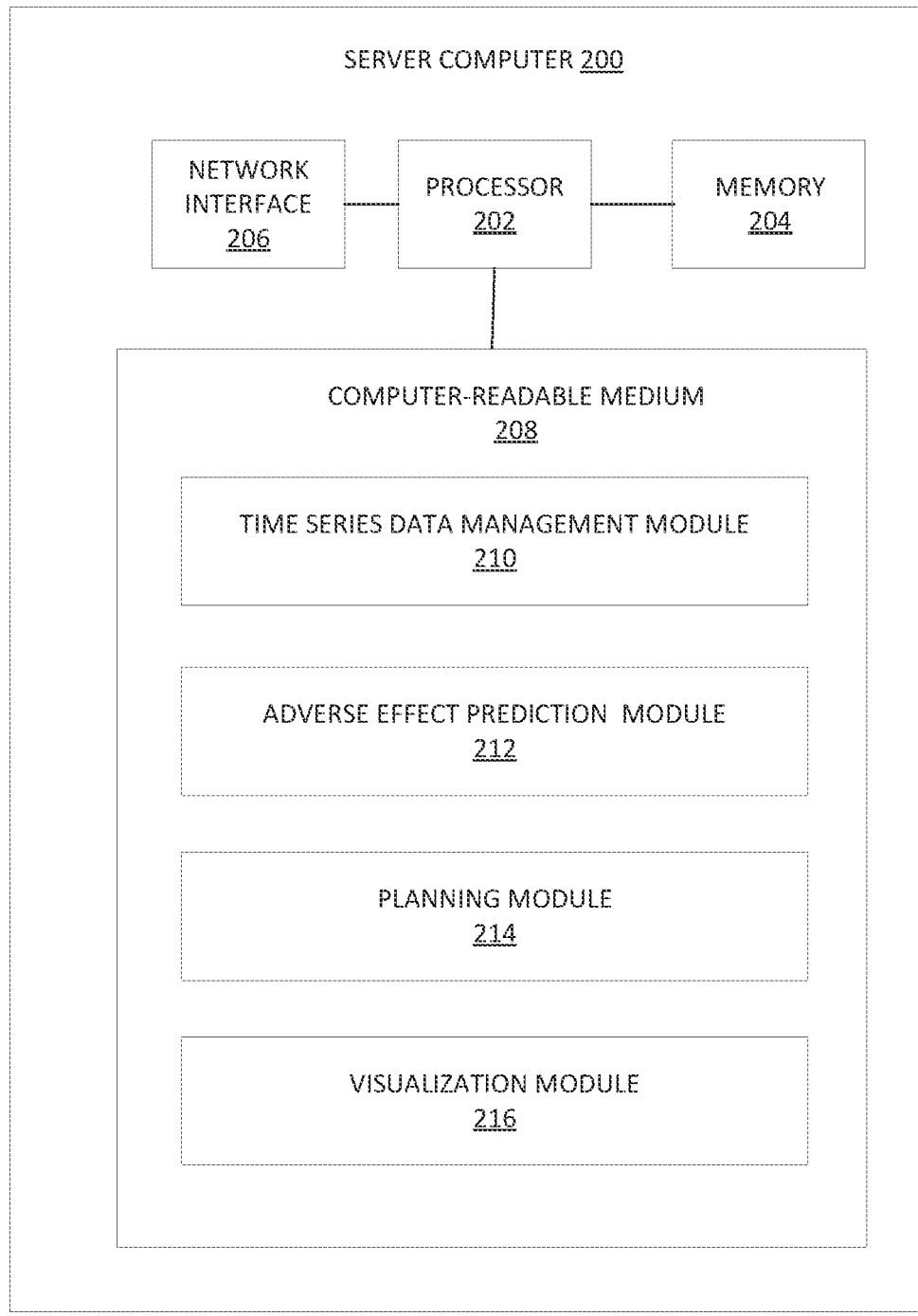
FIG. 2 illustrates a block diagram of the server computer of FIG. 1 according to some embodiments.

FIG. 2 illustrates a server computer 200 according to some aspects of the disclosure. The server computer 200 may, e.g., be the server computer 106 of FIG. 1, The server computer 200 includes functionality to receive and analyze data received from the first user device 104 and/or the wearable device 103. The server computer 200 includes a processor 202 coupled to a memory 204, a network interface 206, and a computer-readable medium 208.

The memory 204 can be used to store data and code. The memory 204 may be coupled to the processor 202 internally or externally (e.g., cloud based data storage), and may comprise any combination of volatile and/or non-volatile memory, such as RAM, DRAM, ROM, flash, or any other suitable memory device. The memory 204 may store user data collected in association with one or more users over time.

The processor 202 may comprise one or more processors, application specific integrated circuits (ASICs), or field programmable gate arrays (FPGAs). The processors may include be single core or multicore processors. In some embodiments, processor 202 can include one or more special purpose co-processors such as graphics processors, digital signal processors (DSPs), or the like. In some embodiments, the processor 202 can be implemented using customized circuits, such as application specific integrated circuits (ASICs), or field programmable gate arrays (FPGAs).

In some embodiments, the processor 202 can execute instructions stored in memory 204 or on computer readable medium 208. In various embodiments, the processor 202 can execute a variety of programs or code instructions and can maintain multiple concurrently executing programs or processes. At any given time, some or all of the program code to be executed can be resident in memory 204 and/or on computer-readable medium 208 including potentially on one or more storage devices. Through suitable programming, processor 202 can provide various functionalities described above.

The network interface 206 may include an interface that can allow the server computer 200 to communicate with external computers. The computer-readable medium 208 may include software code stored as a series of instructions or commands. The computer-readable medium 208 may comprise code, executable by the processor, to implement methods as described herein.

In some aspects, the computer-readable medium includes a time series data management module 210, an adverse effect prediction module 212, a planning module 214, and a visualization module 216.

The time series data management module 210 includes code for importing, storing, and organizing time series data. In some embodiments, the time series data management module 210 is configured to retrieve data from one or more external devices (e.g., wearable devices, user computing devices, other server computers, etc.). The time series data management module 210 may further be configured to store the time series data in an organized fashion (e.g., in chronological order and/or in association with a user identifier or device identifier).

The adverse effect prediction module 212 includes functionality to predict whether an adverse effect (e.g., an adverse physical effect) is likely, based on analysis of time series data. The adverse effect prediction module 212 may compute one or more values based on retrieved time series data and other data, and use the computed value(s) to predict an adverse effect as described herein.

The planning module 214 includes code configured to generate and update plans for individuals. The plans may be based on factors such as skills to be improved. This can be informed by a skills matrix that takes into consideration factors such as skills needed for a role (e.g., for an athlete, pilot, a particular role in an organization, etc.). The planning may further be based on a predicted adverse effect.

The visualization module 216 includes functionality to generate visualizations, which may include statistics gathered for the individual, plans for the individual, adverse effects predicted, and goals or targets for the individual. The visualizations may further be generated for groups of individuals (e.g., for a team or employer). Examples of such visualizations are illustrated in FIGS. 5A-7E and 9A-10B.

Figure 3:
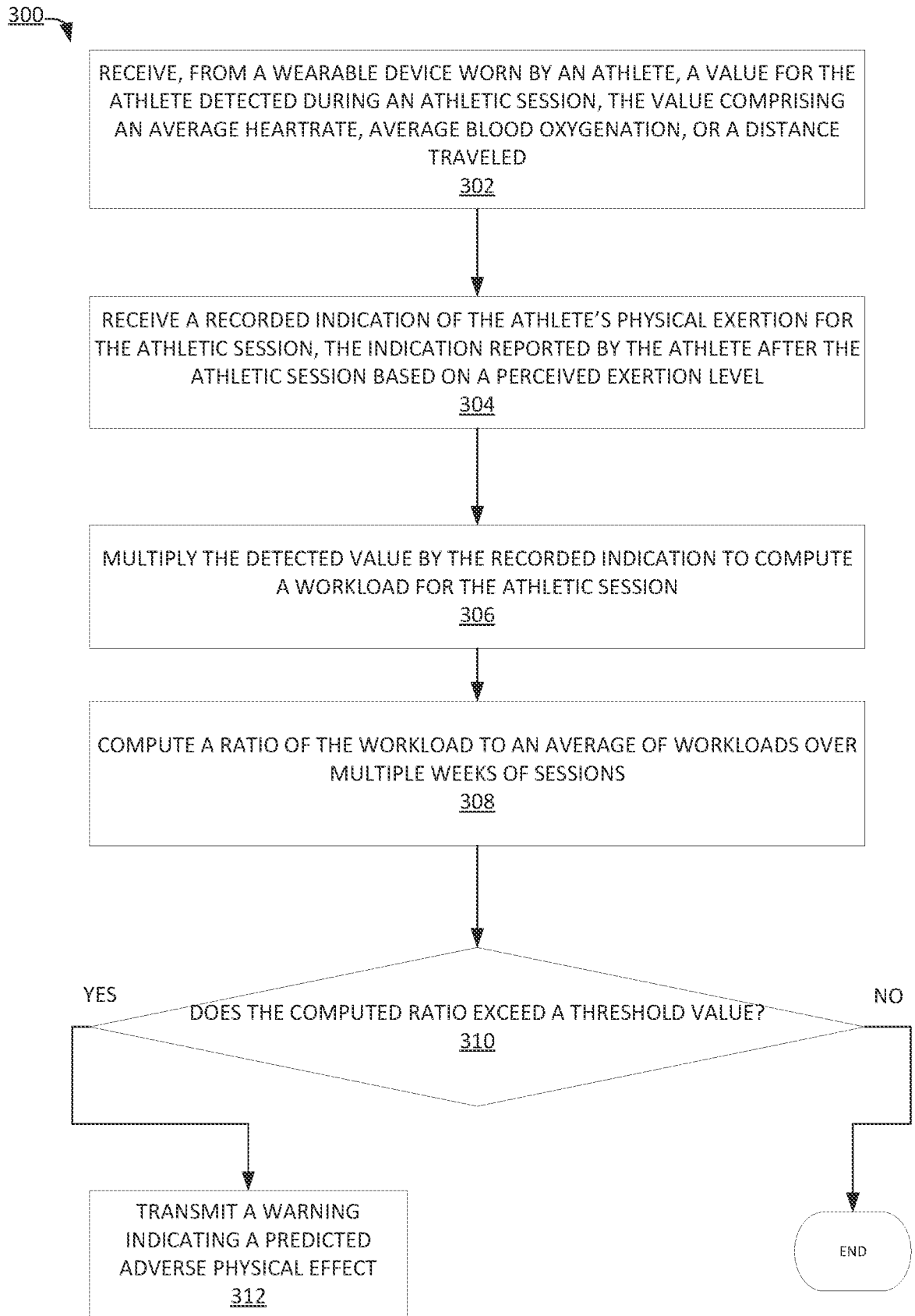
FIG. 3 is a flow chart illustrating a method for predicting an adverse physical effect according to some embodiments.

FIG. 3 is a flow chart illustrating a method 300 for predicting an adverse physical effect according to some embodiments. The method 300 may be performed by the server computer, in cooperation with other components of the system of FIG. 1. The method 300 presented in FIG. 3 and described below is intended to be illustrative and non-limiting. Although FIG. 3 depicts the various processing steps occurring in a particular sequence or order, this is not intended to be limiting. In certain embodiments, the steps may be performed in different order or some steps may be performed in parallel.

At step 302, the server computer receives, from a wearable device worn by an athlete, a value for the athlete detected during an athletic session. The server computer may receive one or more values from a wearable device over a network via a wireless or wired connection. The values may be received directly from the wearable device or via a user device coupled to the wearable device. The value may include an average heartrate, an average blood oxygenation, and/or a distance traveled. In some embodiments, the values are transmitted as time series data. For example, each value is associated with a corresponding time stamp (e.g., at t=1, heart rate=100 beats per minute, at t=2, heart rate=120 beats per minute, and so forth).

As a specific example, a group of players on a sports team each wear a biometric and GPS tracking vest during training and games. These vests record a myriad of data-points for each wear session: average, minimum, a maximum heart rate; time in each heart rate zone (1-5); distance travelled; number of sprints; average, min, max speed; etc. This data is transmitted to, and received by, the server computer for further processing.

In some embodiments, the server computer may compute an intermediate value based on received data. For example, the server computer receives timestamped data such as heartrate data or blood oxygenation data. The server computer averages the timestamped heartrate data over some time period or timestamped blood oxygenation data in order to calculate an average heartrate or an average blood oxygenation over that time period.

At step 304, the server computer receives a recorded indication of the athletes physical exertion for the athletic session. The recorded indication may, for example, be a rating based on a subjective perception of an exertion level. For example, the indication is a number on a scale from one to ten, zero to one hundred, etc. In some aspects, the indication is reported by the athlete after the athletic session based on a perceived exertion level. For example, the athlete may interact with an interface on a user device, as illustrated in FIGS. 5B and 5C. As a specific example, the athlete may type in or interact with a slider to select "80" out of 100 to represent that the athlete feels a relatively high level of exertion after an athletic session. As another example, a player on a sports team takes a daily survey in the system and the question of importance for this use case is: "Please rate how hard you think you worked at today's session." The answer is a 1 to 10 scale, where 1 is "not hard" and 10 is "strenuous."

Upon receiving the data at steps 302 and 304, the server computer stores the data for the athlete. In some embodiments, this data is fed into the server computer at the end of each athletic session for an athlete. The data is stored in association with a particular athlete (e.g., indexed with a user identifier).

At step 306, the server computer multiplies the detected value by the recorded indication to compute a workload for the athletic session. In some aspects, the server computer retrieves one or more stored values and matches the values based on a common identifier. For example, the detected value and the recorded indication may be stored to a database indexed using a unique identifier of the athlete. The server computer may use such a user identifier to identify and retrieve corresponding values. The server computer then computes the workload by multiplying the identified value by the reported indication. As an example, the data received at step 304 is a daily answer submitted by the athlete indicating a perceived exertion level for the athletic session, and the data received at step 302 is a distance traveled in a daily workout session. The system multiplies the daily answer by the distance traveled to compute a work load value for the athletic session.

At step 308, the server computer computes a ratio of the workload to an average of workloads over multiple weeks of sessions. The server computer may compute a "chronic workload" by computing the average of workloads over multiple sessions (e.g., workload value 1+workload value 2+ . . . workload value n, divided by n, where n is the number of sessions in a three-week period). The server computer may then compute an ACWR by dividing the workload value computed at step 306 by the chronic workload value.

Studies have shown that, when a workload value for a current session exceeds a certain multiple of the chronic work load, the player may be at risk for a non-contact injury, like a muscle or ligament strain. Thus, the ACWR can be used to identify when the player is at risk for non-contact injury. In some aspects, after the data for each session is loaded into the system at steps 302 and 304, the server computer automatically calculates the ACWR for the current session.

At step 310, the server computer determines whether the computed ratio exceeds a threshold value. In some aspects, the server computer maintains one or more stored threshold values. In some embodiments, the threshold is configurable (e.g., via a user interface). For example, the system provides a dashboard to an administrator (e.g., the captain of a sports team). Using the dashboard, the administrator can specify a threshold (e.g., a "multiple" in the example above). This threshold is then used in order to best approximate the administrator's tolerance for risk and desire to manage injury prevention. In some embodiments, the server computer sets a default threshold value of 1.5. The server computer may identify the appropriate threshold value and compare the threshold value to the ratio computed at step 308.

At step 312, if the server computer determines that the computed ratio exceeds the threshold value at 310, then the server computer transmits a warning indicating a predicted adverse physical effect. For example, if the ACWR for a given player exceeds the "multiple" specified in the system by the staff, the staff is alerted that the given player may need attention or treatment. In some embodiments, the warning is transmitted via an electronic mail (email) or text message. The warning may include a message such as "Warning—ACWR high," "Alert—injury likely given exertion level," "Rest recommended," and so forth. In some embodiments, the email message or text message further includes supplementary information, which may include information determined by the server computer in making the determination to transmit the warning. Such supplementary information may include average heartrate, average blood oxygenation, distance traveled, and so forth. In some aspects, a first email is sent to the athlete, including the average heartrate, the average blood oxygenation, or the distance traveled. The server computer prepares a second email message, the second email message identifying the athlete but omitting the average heartrate, the average blood oxygenation, or the distance traveled. The second email is sent to another party such as a coach of the athlete. Alternatively, or additionally, the warning may be transmitted as an in-application alert (e.g., via an interface such as those shown in FIGS. 5A-7E).

In some embodiments, in addition to, or alternatively to, transmitting the warning, the system updates a schedule of the athlete responsive to determining that the ratio exceeds the threshold. The system may maintain, or be coupled to, a calendar of the athlete. The system may modify the calendar of the athlete. For example, the server computer modifies a calendar of the athlete to remove a training session, so that the athlete is not as likely to be overexerted which could potentially lead to injury. Alternatively, or additionally, the server computer replaces a first type of training session with a second type of training session. For example, the server computer replaces a high impact activity such as tackling practice with a low impact activity such as stretching to reduce the likelihood of injury.

In some embodiments, the calendar is modified in the context of a training matrix. As illustrated in FIG. 9C, the server computer may manage a training matrix (e.g., a skills matrix for an athlete) based on a position or role of the athlete. For example, a quarterback may have training goals such as a certain passing completion rate and a certain sprinting speed. These training goals can be represented as a skills matrix, as further described below with respect to FIGS. 8 and 9D. The server computer may search the training matrix based on the position or role of the athlete. For example, the server computer maintains training matrixes based on different positions such as quarterback, kicker, and so forth. The server computer accesses the calendar for the athlete (e.g., within its own system or via an Application Programming Interface (API) connection to an external calendar). The server computer may then compare at least one training session in the calendar to recommendations in the training matrix. For example, the training matrix recommends three passing drills a week. Accordingly, the server computer searches the week's calendar entries for the athlete to determine whether additional training sessions should be scheduled. If additional training sessions should be scheduled, or removed, or modified, then the server computer modifies the calendar based on the comparison.

FIG. 4 is a flow chart illustrating a method 400 for predicting an adverse physical effect according to some embodiments. The method 400 may be performed by the server computer, in cooperation with other components of the system of FIG. 1. The method 400 presented in FIG. 4 and described below is intended to be illustrative and non-limiting. Although FIG. 4 depicts the various processing steps occurring in a particular sequence or order, this is not intended to be limiting. In certain embodiments, the steps may be performed in different order or some steps may be performed in parallel.

At step 402, the server computer receives a first data set. The first data set may be received from a user device (e.g., first user device 104 and/or second user device 108 of FIG. 1). The first data set may be received by the server computer from the user device over a network (e.g., via a wireless or wired connection). The first data set comprises a first plurality of timestamps, an identifier of an individual, and a plurality of first measurements.

Each data set may include a plurality of measurements. Each measurement represents a measurement at a particular time, and may be associated with a timestamp. Each data set may also include an identifier of the user and/or user device (e.g., a Universally Unique Identifier (UUID), user name, first and/or last name, nickname, IP address, and so forth). For example, a data set may be:

| Name | Time | Heart Rate |
| --- | --- | --- |
| John Smith | Jan. 1, 2019 12:00:01 | 90 |
| John Smith | Jan. 1, 2019 12:00:31 | 91 |
| John Smith | Jan. 1, 2019 12:01:01 | 85 |
| John Smith | Jan. 1, 2019 12:01:31 | 82 |
| John Smith | Jan. 1, 2019 12:02:01 | 77 |

At step 404, the server computer receives a second data set. The second data set comprises a plurality of second timestamps, the identifier of an individual, and a plurality of second measurements. The second data set may correspond to the same individual that the first data set of step 402 corresponds to, but at a later time. The server computer receives the second data set in a similar fashion as receiving the first data set at step 402.

At step 406, the server computer correlates the first data set and the second data set based on the identifier of the individual, the plurality of first timestamps, and the plurality of second timestamps. The server computer may determine that the first data set and the second data set are both stored in association with the same identifier of the individual. The server computer may correlate the data sets by storing the data sets in association with one another (e.g., in a table as shown above). Alternatively, or additionally, the server computer may correlate two previously stored data sets by retrieving the two data sets (e.g., by querying a database on the identifier of the individual). In any event, the server computer identifies that the two data sets correspond to the same individual and selects the first data set and the second data set for further processing.

At step 408, based on the correlated first data set and second data set, the server computer predicts an adverse physical effect. In some embodiments, the server computer predicts the adverse physical effect by computing a value and comparing the value to a threshold. For example, the server computer computes an acute chronic workload ratio, as described above with respect to steps 306 and 308 of FIG. 3, then compares the acute chronic workload ratio to a predetermined threshold value, as described above with respect to step 310 of FIG. 3. If the acute chronic workload ratio, or another suitable value, exceeds a threshold, then the server computer may predict that an adverse physical effect is likely to occur.

At step 410, the server computer transmits a warning of the adverse physical effect. The server computer may transmit the warning in a similar fashion as described above with respect to step 312 of FIG. 3.

FIGS. 5A-5D illustrate example user interfaces for displaying and accepting user data according to some embodiments. The interfaces of FIGS. 5A-5D may be displayed to a user whose data is being analyzed—e.g., user 102 of FIG. 1, via first user device 104 of FIG. 1.

Figure 5A:
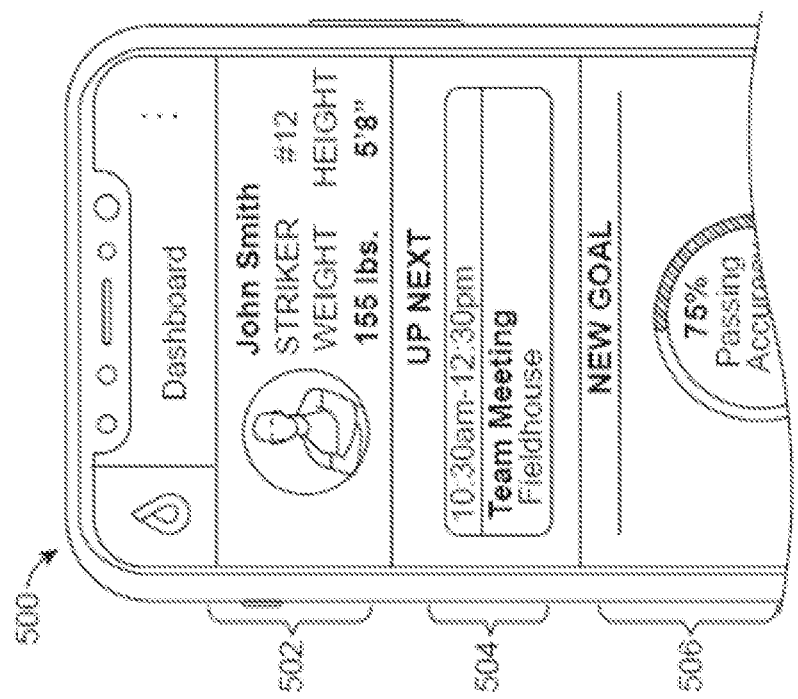
FIG. 5A illustrates an example user interface for accepting user data according to some embodiments.

FIG. 5A illustrates a user interface 500 for displaying user information. The user interface 500 may be a graphical user interface (GUI). The user interface 500 may show statistics about the user 502 (e.g., name, team number, weight, height, and so forth). The user interface 500 may show scheduling information 504 (e.g., team meeting at 10:30 AM). The user interface 500 may show player statistics and/or goals 506 (e.g., a goal to improve passing accuracy by a certain percentage. The user interface 500 may show progress towards such a goal, tips for reaching a goal, and so forth.

FIG. 5B illustrates a user interface 520 for receiving user information. The user interface 520 may be a graphical user interface (GUI). The user interface 520 may include elements for receiving input from a user. As shown in FIG. 5B, the user interface 520 includes a slider bar 522 and the text 524 "Rate your nutrition today." The user interface 520 may receive user input via the slider bar 522 rating the user's perceived nutrition on a scale from 1 to 5 (a "nutrition score"). In this example, the nutrition score selected is 5, indicating a very good nutrition score.

FIG. 5C illustrates a user interface 540 for receiving user information. The user interface 540 may be a graphical user interface (GUI). The user interface 540 may include elements for receiving input from a user. As shown in FIG. 5C, the user interface 540 includes a slider bar 542 and the text 544 "rate how rested do you feel today." The user interface 540 may receive user input via the slider bar 542 rating the user's perceived rest level on a scale from 1 to 5. In this example, the user has selected 1, indicating they do not feel very well rested.

The information received from user interfaces 520 and 540 may be analyzed by server computer 106 of FIG. 1. For example, the nutrition data may correspond to the first data set, and the server computer 106 may store and analyze a plurality of data points corresponding to the user provided nutrition score, along with timestamps for each respective data point and a user identifier identifying the corresponding user.

Figure 5D:
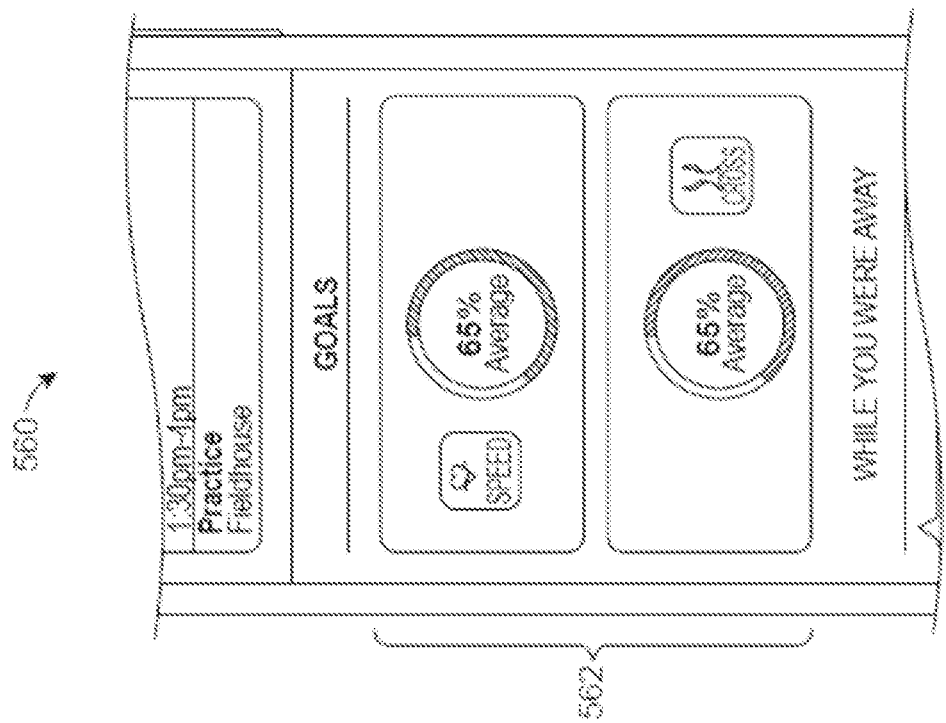
FIG. 5D illustrates an example user interface for displaying user information according to some embodiments.
Figure 5C:
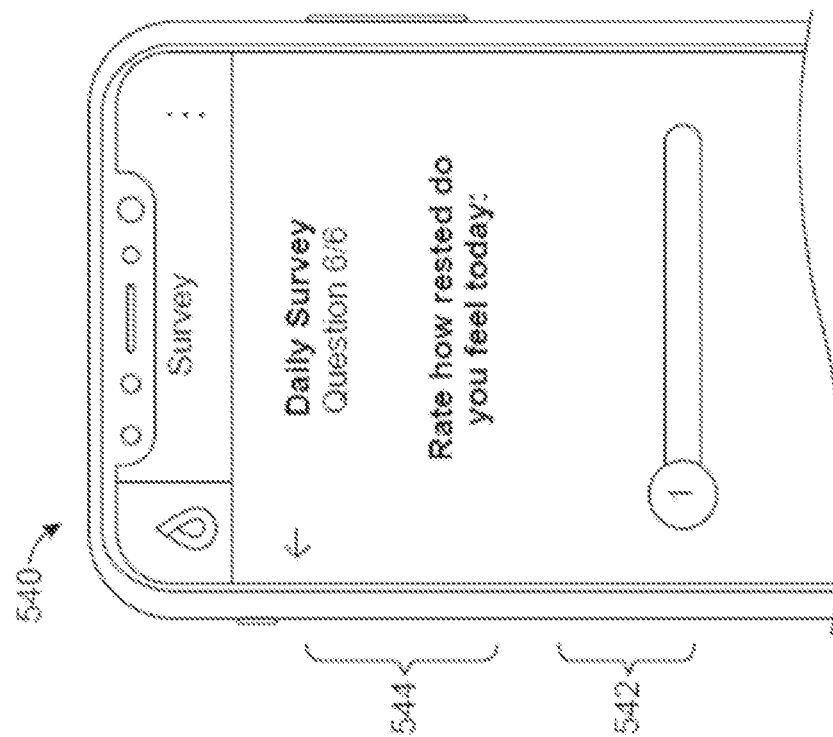
FIG. 5C illustrates another example interface for receiving user information according to some embodiments.

FIG. 5D illustrates a user interface 560 for displaying user information. The user interface 560 may be a graphical user interface (GUI). The user interface 560 may include elements for displaying information to a user. As shown in FIG. 5D, the user interface 560 displays two goals 562—"speed" and "cross" along with a percentage indicator for each showing how far the user has currently progressed towards achieving the respective goals.

Figure 6:
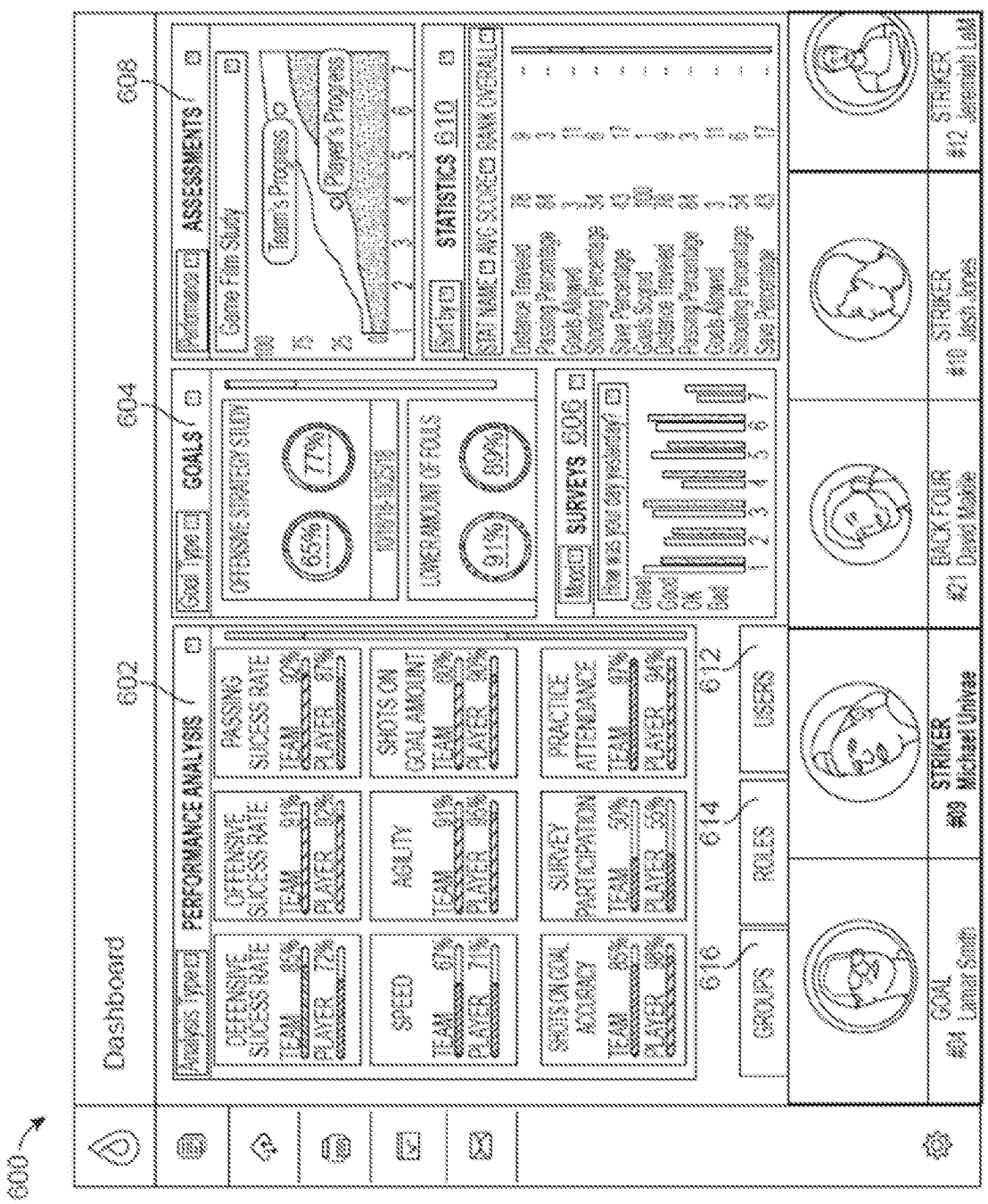
FIG. 6 illustrates an example dashboard interface according to some embodiments.

FIG. 6 illustrates an example dashboard interface 600 according to some embodiments. The dashboard interface 600 may, for example, be displayed via second user device 108 of FIG. 1. As indicated in FIG. 6, the dashboard interface 600 may display information about a team to a manager. The dashboard interface 600 may display overall statistics about a sports team, infantry unit, work team, and so forth. The dashboard interface 600 may allow a user to drill down into different statistics, groups, and/or users. The dashboard interface 600 includes a performance analysis section 602, showing statistics for a group of users such as defensive success, passing success, speed, and agility. The dashboard interface 600 includes a goals section 604, showing how far along a group of users is with certain goals such as lower amount of fouls. The dashboard interface further includes surveys 606, assessments 608, and statistics 610 for the team as a whole. A coach or other entity can interact with these elements to drill down into a particular category of information and/or information about a particular athlete. Different selectable users 612 (e.g., athletes on the team), roles 614, and groups 616 are also displayed.

FIGS. 7A-7E illustrate example user interfaces illustrating first data and second data over time for several different users. The user interfaces of FIGS. 7A-7E may, for example, be displayed via second user device 108 of FIG. 1. The user interfaces of FIGS. 7A-7E may display information about team members to an entity such as a team manager or coach.

In FIGS. 7A-7E, user interfaces are displayed showing a visualization of time series data 701 for different team members 703. On the left side is a list of athletes/team members 703. A user (e.g., an administrator, coach, etc.) may interact with the names of the team members 703 to initiate display of detailed information about that team member. The interfaces of FIGS. 7A-7E illustrate time series data corresponding to three different data sets—zone 5 705, or heartrate data, ACWR 707, and acute work load 709. At the bottom, dates 711 are shown. The dots above the dates are blue if data has been received for that data for that athlete, and white if data has not been received for that date for that athlete. By each athlete's name is a color code indicating whether an adverse effect is predicted or has occurred, which can be determined using the techniques described above with respect to FIGS. 3 and 4.

Figure 7A:
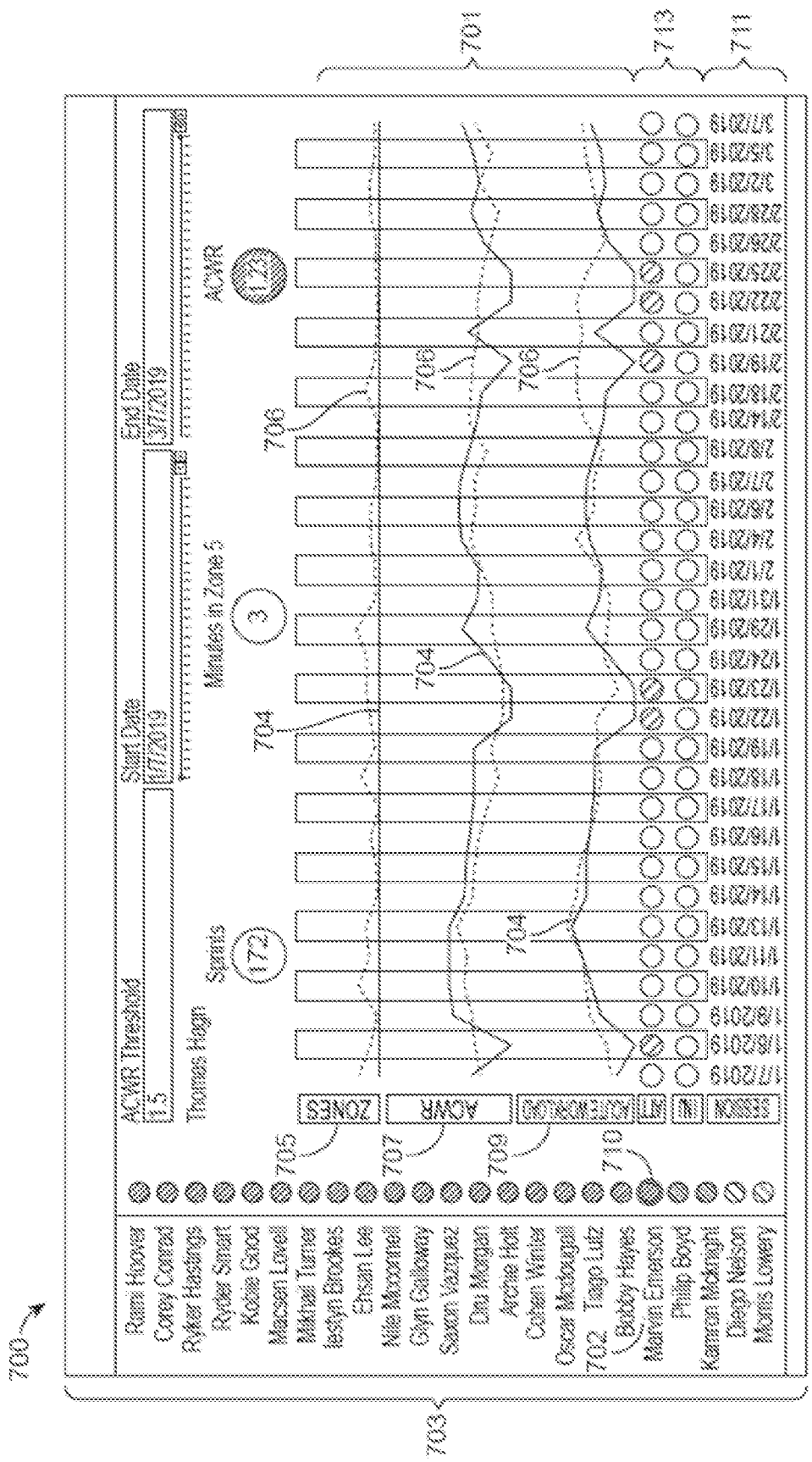
FIG. 7A illustrates an example user interface illustrating first data and second data over time for a first user, according to some embodiments.

FIG. 7A illustrates a user interface 700 illustrating data sets over time for a first athlete, Marvin Emerson 702. The solid lines 704 represent Marvin Emerson's data, and the dotted lines 706 represent average data for the team. Marvin Emerson's zone 5/heartrate 705, ACWR 707, and acute work load 709 data are generally near or below the average. Based on analyzing Marvin Emerson's data, the server computer has determined that, for Marvin Emerson 702, an adverse physical effect (e.g., injury) is not likely. Accordingly, the color code 710 for Marvin Emerson is green to indicate he is not currently at heightened risk of injury.

Figure 7B:
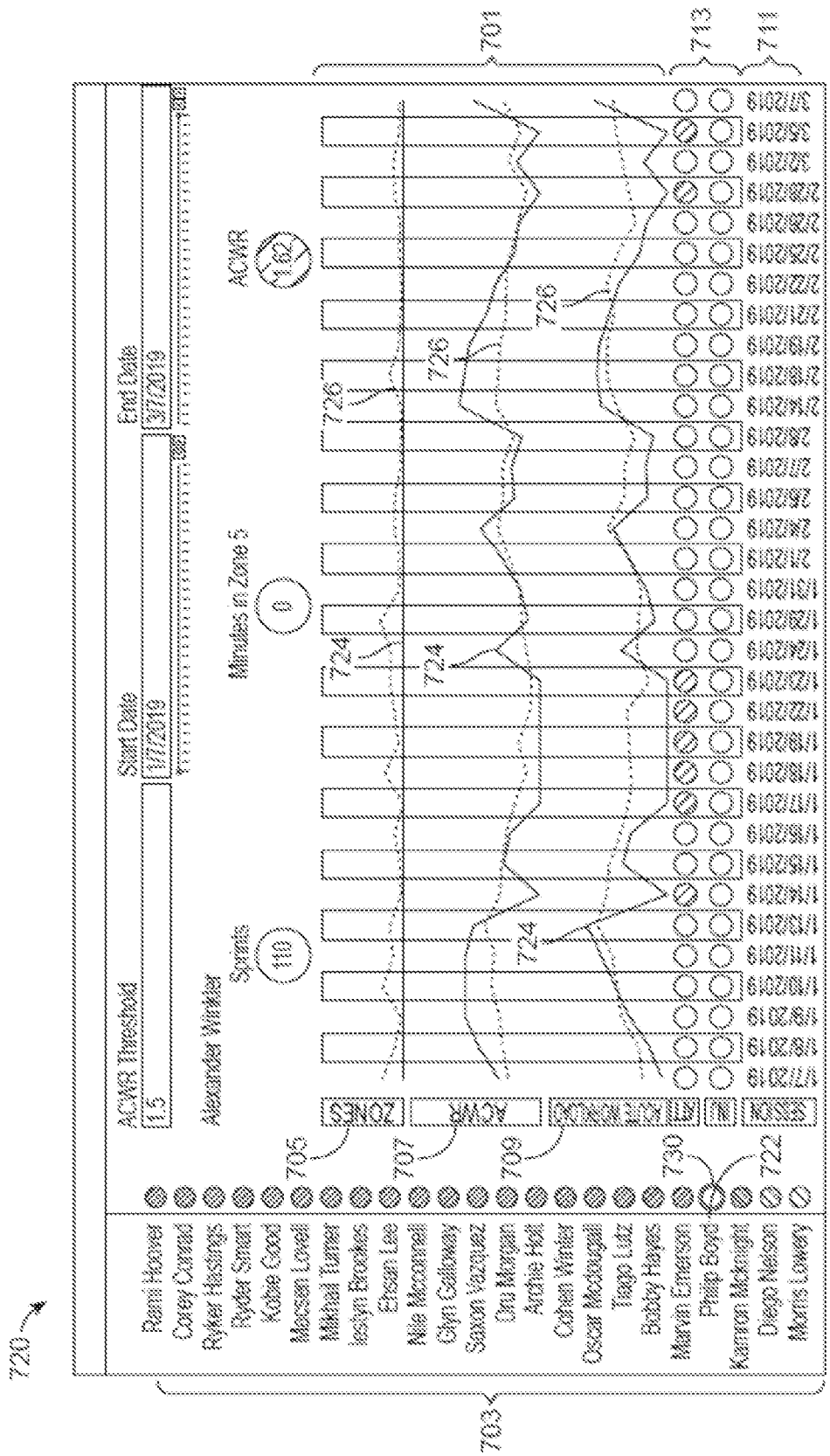
FIG. 7B illustrates an example user interface illustrating data sets over time for a second user, according to some embodiments.

FIG. 7B illustrates a user interface 720 illustrating data sets over time for a second athlete, Philip Boyd 722. The solid line 724 represents Philip Boyd's data, and the dotted lines 726 represent average data for the team. Philip Boyd's zone 5/heartrate 705, ACWR 707, and acute work load 709 data are generally near or below the average, but the ACWR 707 and acute work load 709 data for Philip Boyd exhibit spikes above the average. Based on analyzing Philip Boyd's data, the server computer has determined that an adverse physical effect (e.g., injury) is likely for Philip Boyd. Accordingly, the color code for Philip Boyd 722 is yellow 730 to indicate he is at heightened risk of injury.

Figure 7C:
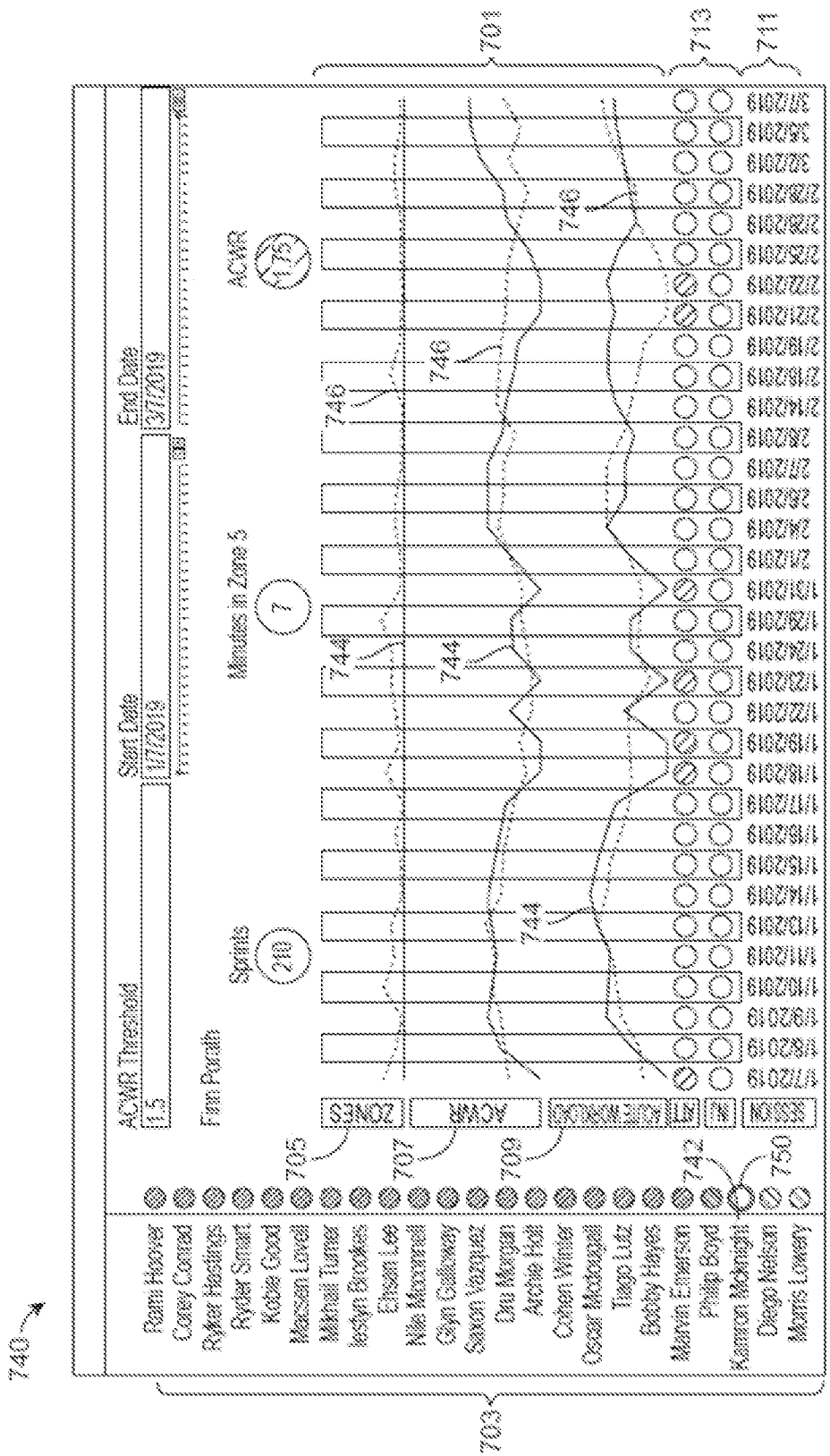
FIG. 7C illustrates an example user interface illustrating data sets over time for a third user, according to some embodiments.

FIG. 7C illustrates a user interface 740 illustrating data sets over time for a third user, Kamron Mcknight 742. Similarly to the user interface 720 corresponding to Philip Boyd, Kamron Mcknight is at heightened risk of injury based on his zone 5 705, ACWR 707, and acute work load data 709 (indicated by the corresponding solid lines 744, as compared to the respective team average data 746). Accordingly, the color code next to Kamron Mcknight's name 742 on the left hand side of the user interface is yellow 750.

Figure 7D:
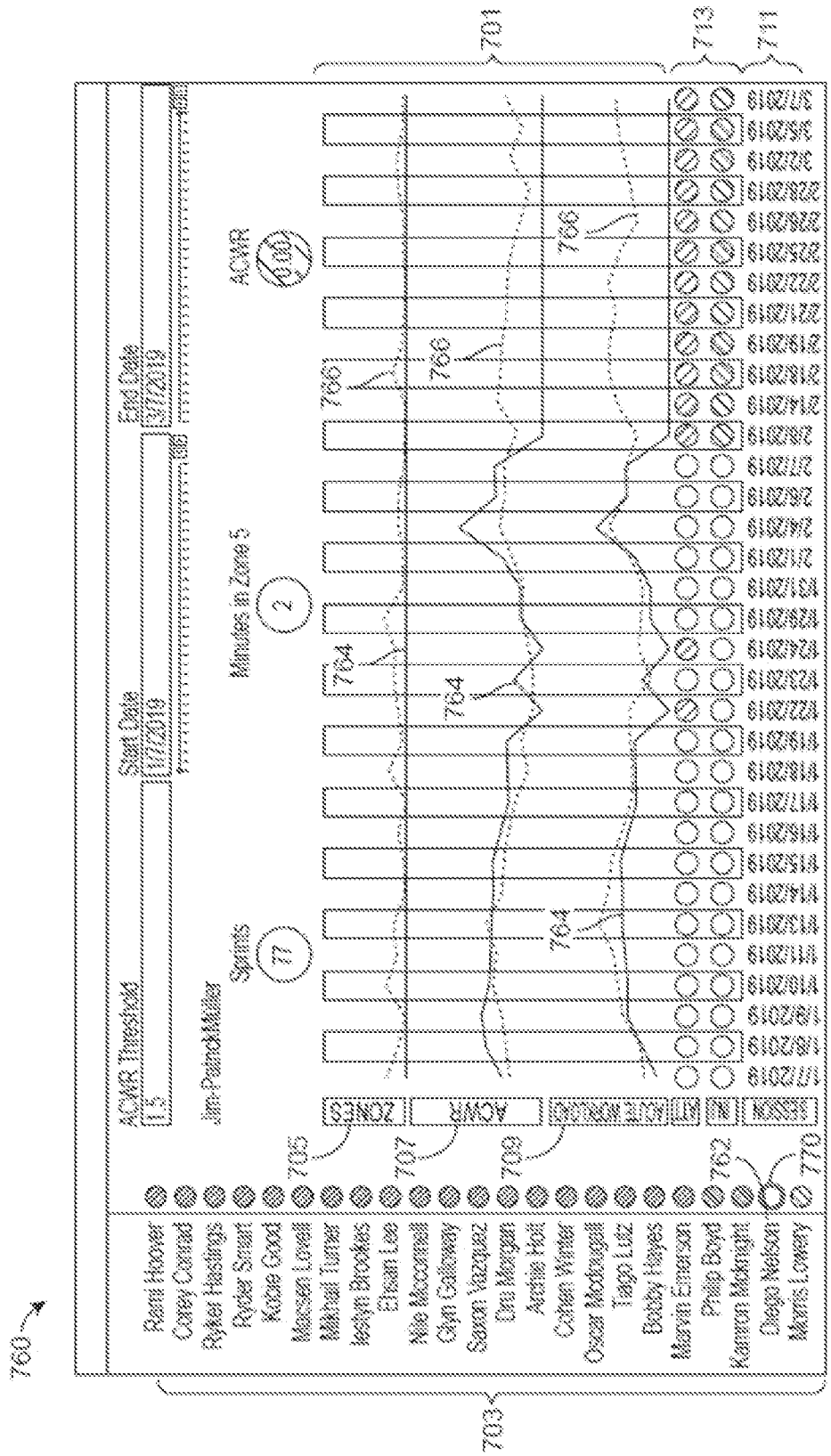
FIG. 7D illustrates an example user interface illustrating data sets over time for a fourth user, according to some embodiments.

FIG. 7D illustrates a user interface 720 illustrating data sets over time for a fourth user, Diego Nelson 762. The solid lines 764 represent Diego Nelson's data, and the dotted lines 766 represent average data for the team. Diego Nelson's ACWR 707 and acute work load data 709 exhibit spikes above the average. Based on analyzing Diego Nelson's data, the server computer has determined that an adverse physical effect (e.g., injury) is likely. Further, Diego Nelson actually had an injury. For such cases where an injury occurred, the system displays a red color code 770, as indicated in FIG. 7D.

Figure 7E:
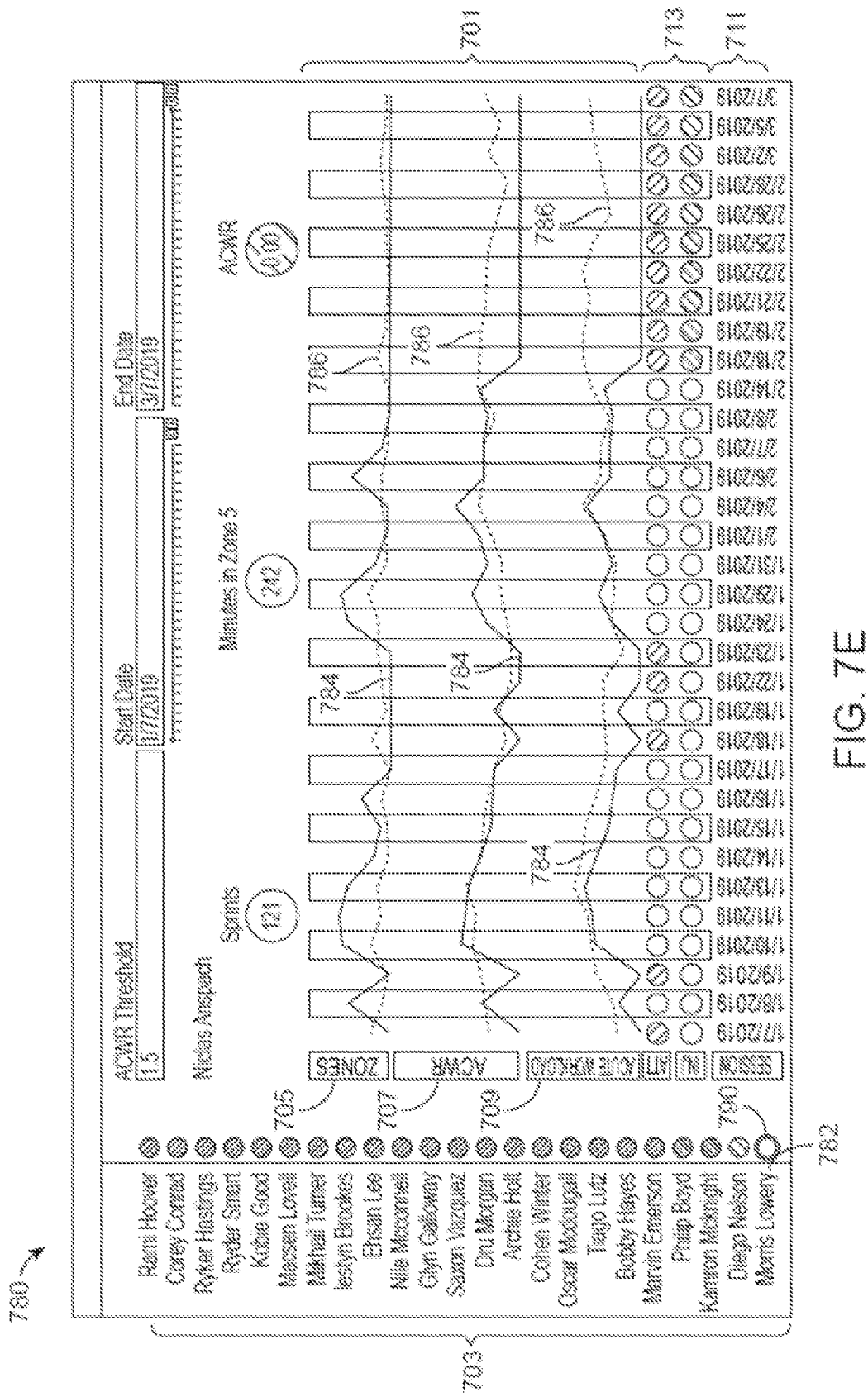
FIG. 7E illustrates an example user interface illustrating data sets over time for a fifth user, according to some embodiments.

FIG. 7E illustrates a user interface 780 illustrating data sets over time for a fifth user, Morris Lowery 782. Morris Lowery's time series data 784 trends high, compared to the team average time series data 786. Further, Morris Lowery 782 has been injured. Accordingly, the color code next to Diego Nelson's name on the left hand side of the user interface is red 790.

Figure 8:
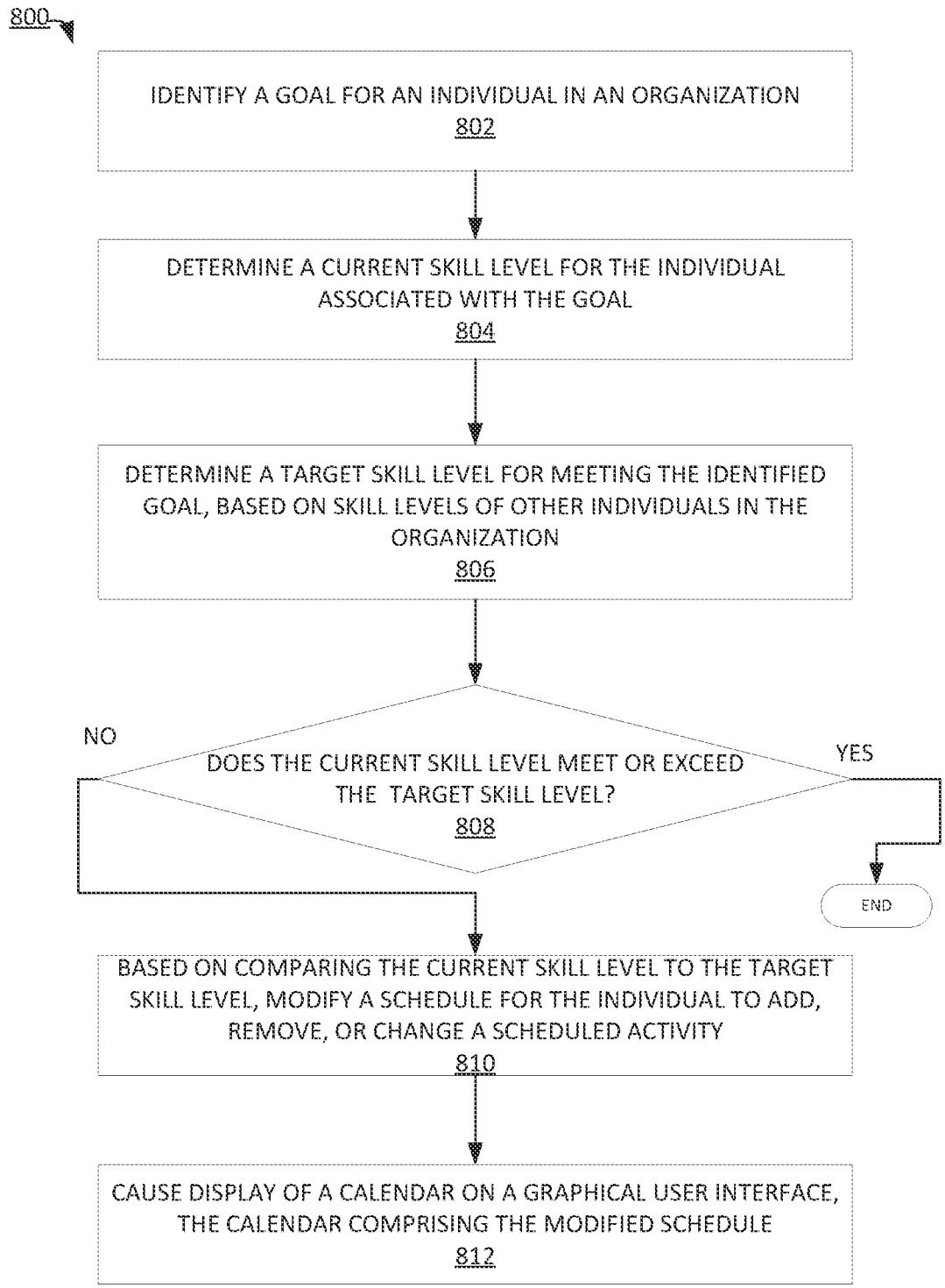
FIG. 8 is a flow chart illustrating a method for identifying activities for meeting a goal according to some embodiments.

FIG. 8 is a flow chart illustrating a method 800 for identifying activities for meeting a goal according to some embodiments. The method 800 may be performed by the server computer, in cooperation with other components of the system of FIG. 1. The method 800 presented in FIG. 8 and described below is intended to be illustrative and non-limiting. Although FIG. 8 depicts the various processing steps occurring in a particular sequence or order, this is not intended to be limiting. In certain embodiments, the steps may be performed in different order or some steps may be performed in parallel.

At step 802, the server computer identifies a goal for an individual in an organization. The server computer may maintain a set of different roles. Based on such a role, the server computer identifies a goal or set of goals. For example, for the role "baseball player," goals include improving batting percentage and improving catching percentage. For an employee, goals may include improving sales by a certain percentage, completing certain trainings, passing quizzes with a certain pass rate, and so forth. In some embodiments, the server computer may identify such a goal based on a determined role. For example, the server computer first determines a role for the individual (e.g., catcher, editor, pilot, and so forth). Then, based on the identified role, the server computer identifies one or more goals based on the role.

In some embodiments, the goals are managed and identified using a skills matrix. A skills matrix can include an organized set of rules and statistics for managing skill goals within an organization. Using the skills matrix, the server computer may identify one or more goals for the individual. For example, the server computer may navigate the skills matrix, based on identifying the role of quarterback, and identify a set of goals for quarterbacks to achieve.

In some aspects, the skills matrix includes a baseline of where the individual is on track towards perfecting or achieving a role based on competencies and industry standards. The server computer may use the skills matrix to determine a set of steps needed to upskill. This can be weighted across an organization, based on skills necessary for a given function. For example, the server computer traverses the skills matrix to identify 10 skills for a soccer team members generally. In some embodiments, the skills matrix can also be visualized via user interface (e.g., similarly to the user interface illustrated in FIG. 9C).

At step 804, the server computer determines a current skill level for the individual associated with the goal. The server computer may retrieve data stored for the individual such as time-series data or derivatives thereof. For example, after determining a goal of increasing passing percentage, the server computer queries a database to identify the current passing percentage for the individual.

In some embodiments, skills are measured based on proficiency of delivery—e.g., how fast an employee can deliver a goal such as selling 25 mattresses. Alternatively, or additionally, the skills may be measured based on qualitative feedback. For example, a manager or third-party partner may provide feedback indicating that a given individual has the capabilities or skillsets needed. As another example, feedback can be given on a result as a whole (e.g., on the quality of a set of tables produced and shipped to a client). The system can tie feedback back to one or more individuals who worked on a given project.

At step 806, the server computer determines a target skill level for meeting the identified goal, based on skill levels of other individuals in the organization. In some embodiments, the target skill level is determined by the server computer by comparing different individuals within the organization and/or comparing different individuals within other organizations. In some aspects, the server computer uses machine learning to identify characteristic features of individuals who have been associated with success in a role (e.g., an athlete that won a championship, an employee that was promoted, and so forth). Alternatively, or additionally, target goals can be configured by an administrator. For example, a user can configure, view, and manage different targets for individuals within an organization using interfaces such as those shown in FIGS. 9A and 9B.

At step 808, the server computer determines whether the current skill level meets or exceeds the target skill level. The server computer compares the current skill level determined at step 804 to the target skill level determined at step 806 to make the determination.

At step 810, based on comparing the current skill level to the target skill level, the server computer modifies a schedule for the individual. Modifying the schedule for the individual may include adding, removing, and/or changing a scheduled activity. The schedule may correspond to a calendar managed by the server computer. Alternatively, or additionally, the schedule may correspond to a calendar managed by an external application. In this case, the server computer may access and edit the external calendar via an API or other suitable means.

As an example of modifying the schedule, the server computer, upon determining that the individual needs improvement on passing, schedules additional passing drills for the individual. As another example, the server computer may predict an adverse effect (e.g., employee burnout or physical injury, as described above with respect to FIGS. 3 and 4). In this case, the server computer may determine that one or more scheduled activities should be removed from the calendar (e.g., delete 2 workouts from the schedule to avoid physical injury). Alternatively, or additionally, the server computer can change a scheduled activity. For example, upon determining that an athlete is likely to be injured, the server computer modifies the athlete's schedule to replace a sprinting drill with a light stretching session.

At step 812, the server computer causes display of a calendar on a graphical user interface, the calendar comprising the modified schedule. Causing display may include transmitting instructions to an external device (e.g., to a user device over a network), thereby causing the external device to display the calendar on a screen. Alternatively, or additionally, the server computer may itself display the calendar (e.g., on a screen directly coupled to the server computer based on instructions executed by the server computer). Alternatively, or additionally, the server computer can display target goals or events outside of the calendar format, such as using interfaces as shown in FIGS. 10A and 10B.

In some embodiments, the server computer repeats steps 804-812 for two or more skills associated with the goal (e.g., for two skills for improving quarterback performance such as passing and sprinting, or for two skills for improving communication such as speeches and one-on-one interaction). The server computer determines a second current skill level for the individual for a second skill associated with the goal as described above with respect to step 804. The server computer determines a second target skill level for a second skill for meeting the identified goal, based on the skill levels of the other individuals in the organization, as described above with respect to step 806. The server computer compares the comparing the current skill level to the target skill level for the second skill, as described above with respect to step 808. Based on comparing the current skill level to the target skill level for the second skill, the server computer may further modify the schedule for the individual, as described above with respect to step 810.

In some embodiments, one or more of the skills are configured using a graphical user interface (e.g., the same graphical user interface that displays the calendar at step 812, and/or a second graphical user interface different than the graphical user interface that displays the calendar at step 812). For example, in some aspects, the graphical user interface that displays the calendar at step 812 is a first graphical user interface and the skill is a first skill. The first skill and the second skill for meeting the identified goal are configured via input to a second graphical user interface. Interfaces for configuring skills and goals are shown, for example, in FIGS. 9A and 9B. Another user interface with the calendar may, for example, be displayed to the individual on a user device such as the first user device 104 of FIG. 1.

Figure 9A:
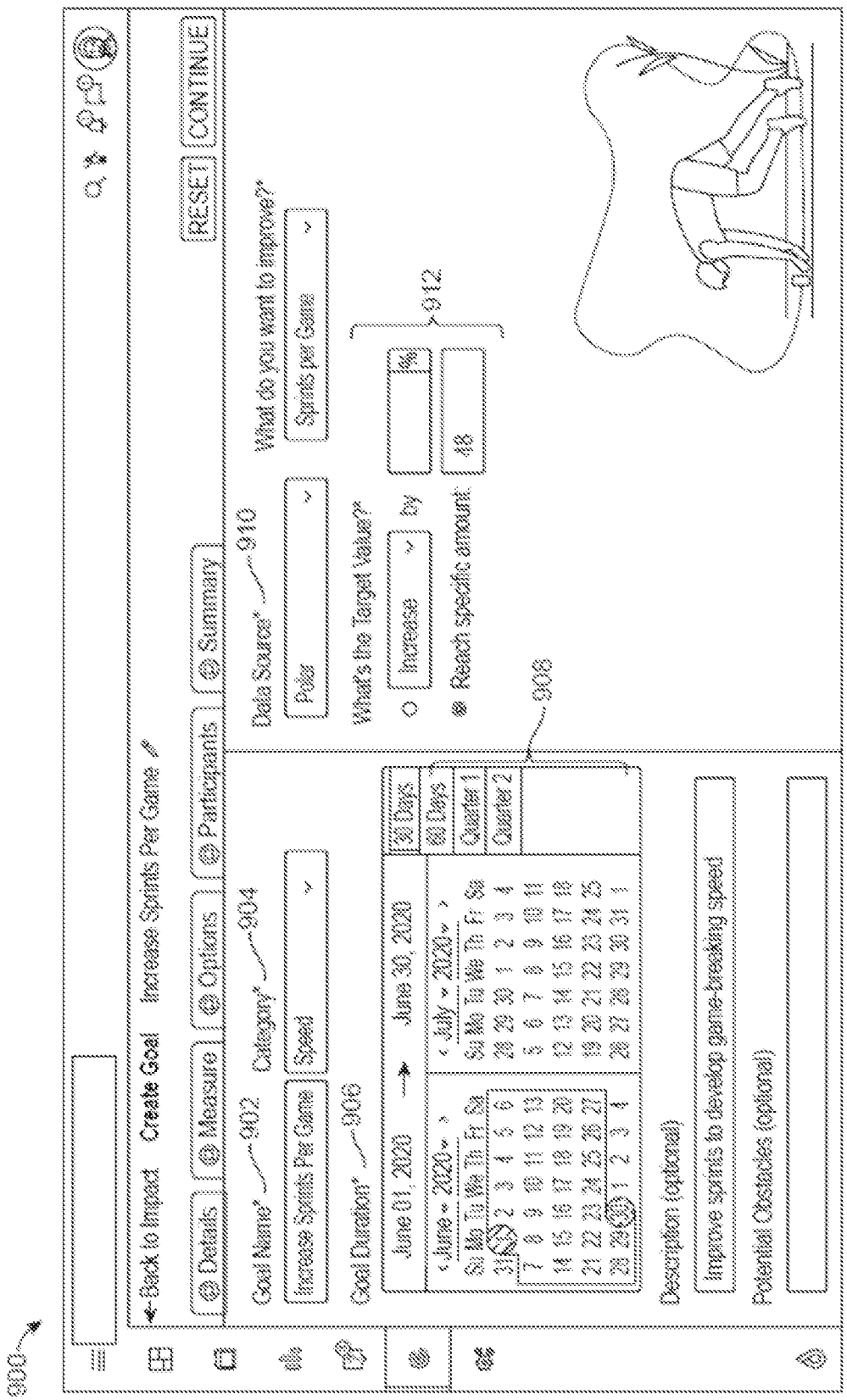
FIG. 9A illustrates an example user interface for accepting goal configuration data according to some embodiments.

FIG. 9A illustrates an example user interface 900 for accepting goal configuration data according to some embodiments. The user interface 900 can be used by a user (e.g., athlete, coach, team manager, etc.) to configure goals for one or more athletes. The user interface 900 includes elements for selecting a goal name 902 (e.g., increase sprints per game) and category 904 (e.g., speed). As shown in FIG. 9A, in this example, the goal name 902 and category 904 can be selected via drop-down menus. The user interface 900 further includes an element for configuring a goal duration 906, including a calendar 908 that a user may interact with to select a time period. The interface further includes an interface element for selecting a data source 910 for collecting time series data (e.g., Polar, a vest) via a drop-down menu. A target value can be selected by elements 912, either by entering an amount to increase the value by, or by entering a specific amount to reach.

Figure 9B:
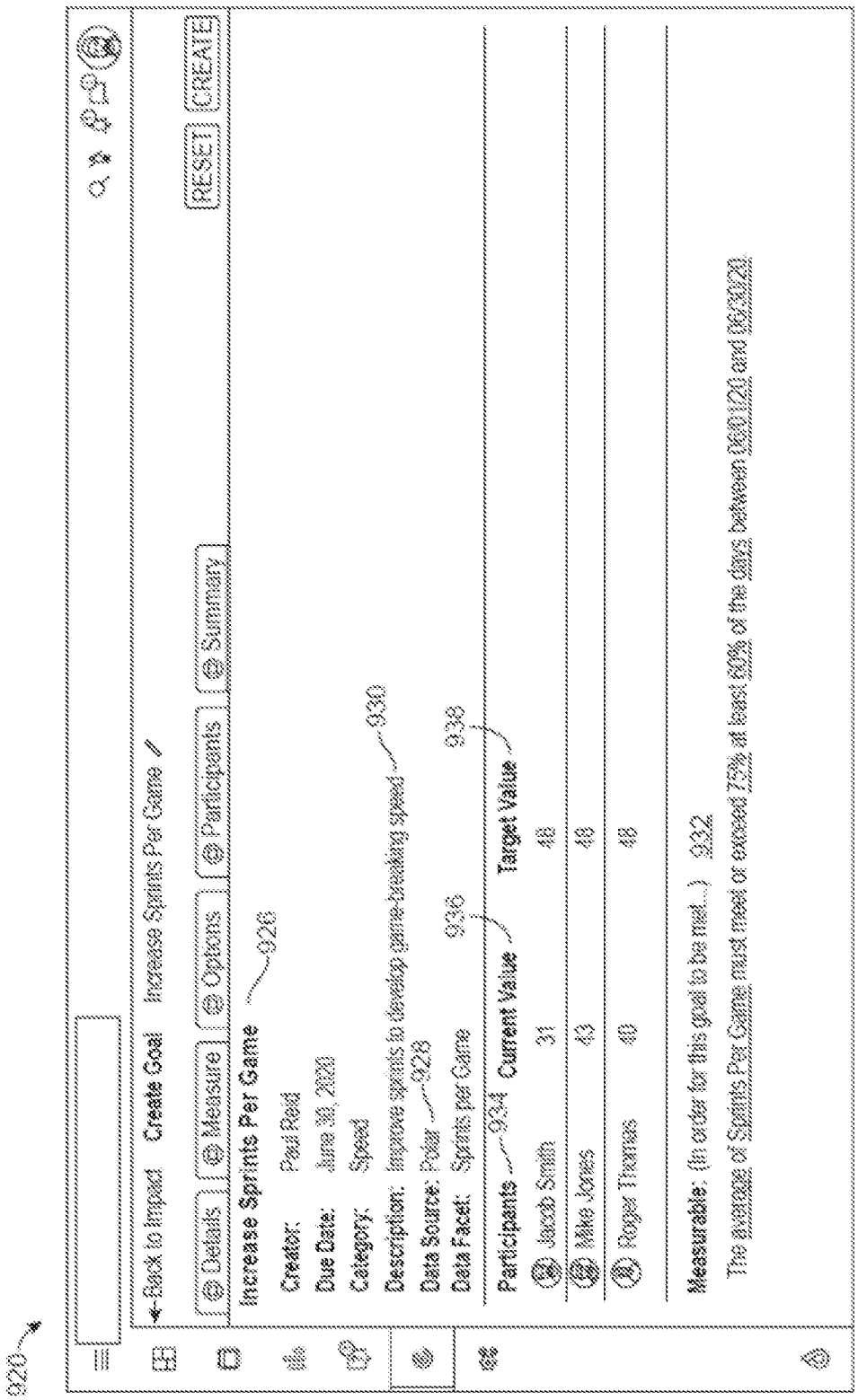
FIG. 9B illustrates an example user interface for displaying goal configuration data according to some embodiments.
Figure 9C:
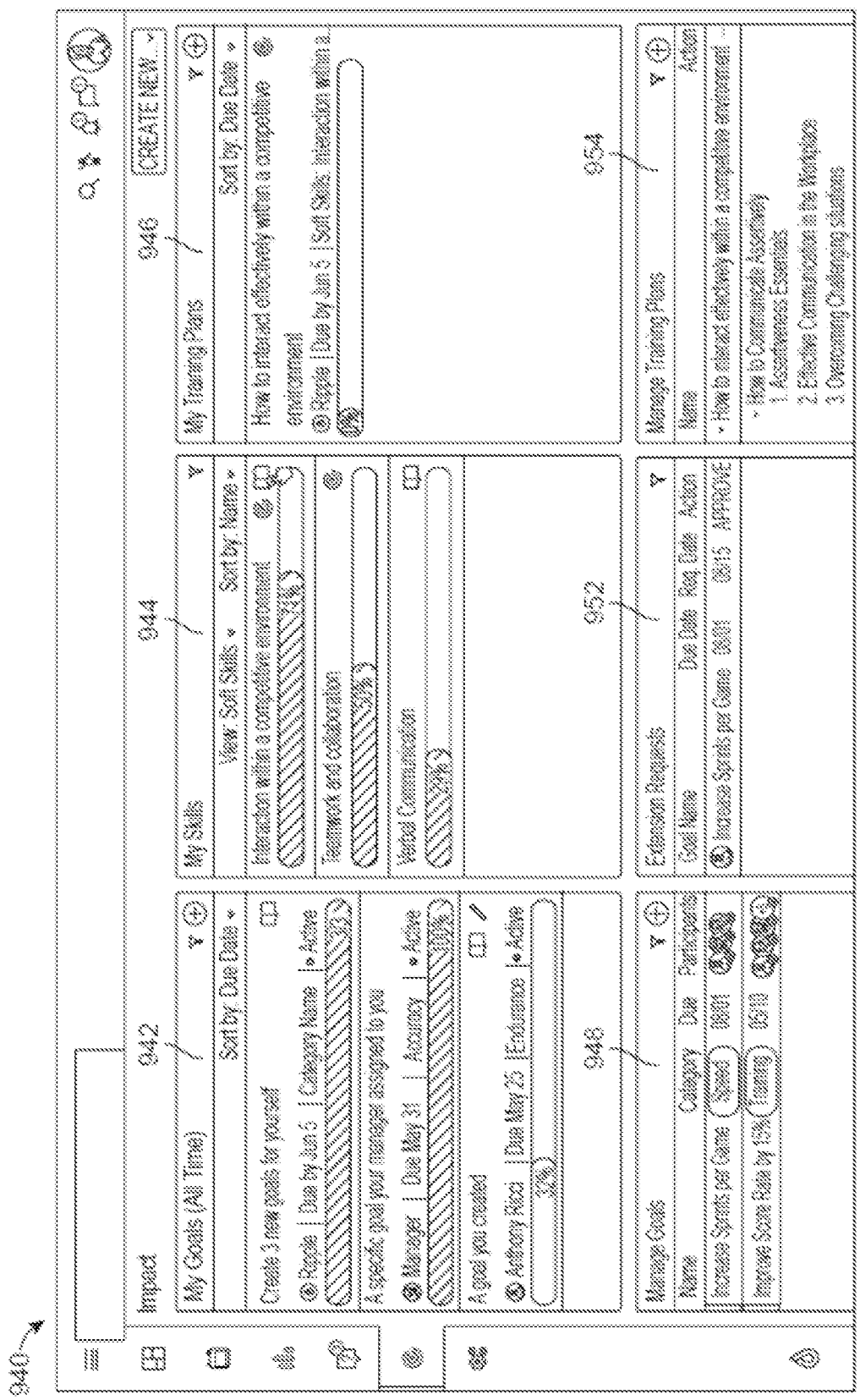
FIG. 9C illustrates an example user interface displaying a visualization of a skills matrix according to some embodiments.

FIG. 9B illustrates an example user interface 920 for displaying goal configuration data according to some embodiments. Interface 920 is a summary view, which may be transitioned to from the configuration view of user interface 900 of FIG. 9A. The user interface 920 shows configuration data and user data for the configured goal "increase sprints per game" 926. The configuration data includes the data source 928, goal description 930, and how the goal is measurable 932. The user data includes the names of participants 934, the current sprints per game value 936 for each participant 934 and the target value 938 for each participant 934.

FIG. 9C illustrates an example user interface 940 displaying an example of a visualization of a skills matrix according to some embodiments. The skills matrix includes a baseline of where a particular individual is on track towards perfecting or achieving a particular role (e.g., within an organization). As described above with respect to FIG. 8, the required competency levels may be determined by the system based on competencies and industry standards. The user interface 940 includes a goals section 942, skills section 944, training plans section 946, goal management section 948, extension request section 950, and training plan management section 952.

The goals section 942 shows a set of goals for the individual—"create 3 new goals for yourself," "a specific goal your manager assigned to you," and "a goal you created," along with a completion percentage for each goal. The skills section 944 illustrates percentage completions for each of a set of soft skills—"interaction within a competitive environment," "teamwork and collaboration," and "verbal communication." The training plans section 946 shows the individual's progress in training plans.

Using the sections 948-952, a user can manage the plans established. Upon detecting user interaction with the goals management section 948, the user interface may transition to a view with interface elements for configuring goals. Goals such as "increase sprints per game" can be added, removed, or modified. The extension requests section 950 includes the name of an extension request (which may have been entered into the system using another interface), a due date, a requested date, and an action. The action is "approve," and the user can interact with the text "approve" to approve the extension request, resulting in modification of the due date to the requested date. The training plans management section 952 includes interface elements for managing training plans. For example, by interacting with the "+" button in the manage training plans section 952, the user can prompt the system to transition to a modified interface view showing a list of additional training plans that can be added. The training plans management section 952 can be used to add, remove, or modify training plans.

Figure 9D:
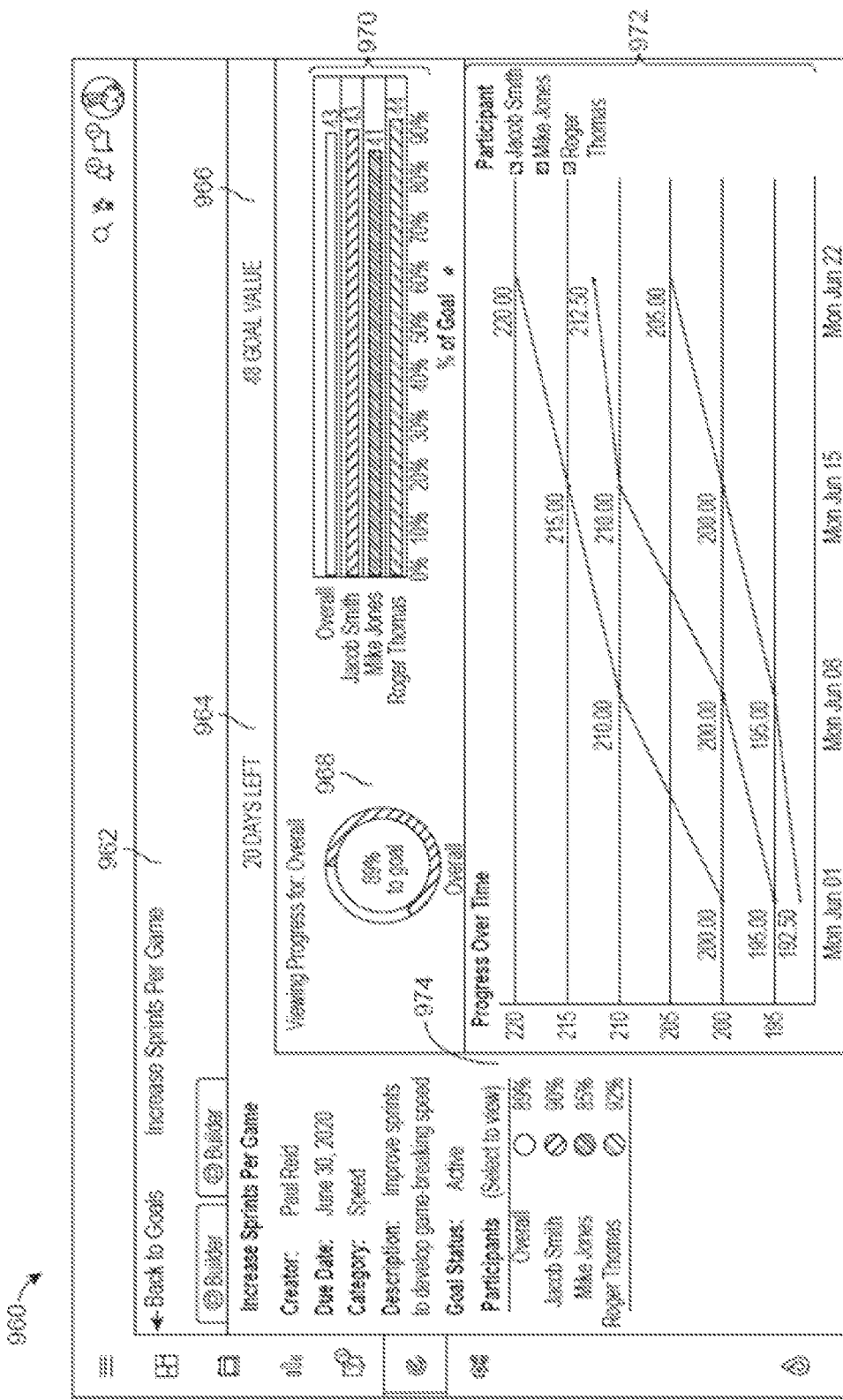
FIG. 9D illustrates an example user interface for displaying progress information according to some embodiments.

FIG. 9D illustrates an example user interface 960 for displaying progress information according to some embodiments. The user interface 960 is for a particular goal 962, increase sprints per game, which is indicated in the user interface 960. The user interface 960 shows the progress towards the goal for a set of individuals. The number of days left 964 for achieving the goal and target goal value 966 are shown.

Element 968 shows a visual representation of overall progress towards a goal for a group of individuals. The overall progress as well as individual progresses of different individuals is shown as a bar graph 970, as well as a graph of progress over time 972. On the left panel, a list of participants 974 is shown. A user can interact with the list of participants 974 to drill down to view progress for a selected individual. This can cause the system to transition to the interface view 980 illustrated in FIG. 9E.

Figure 9E:
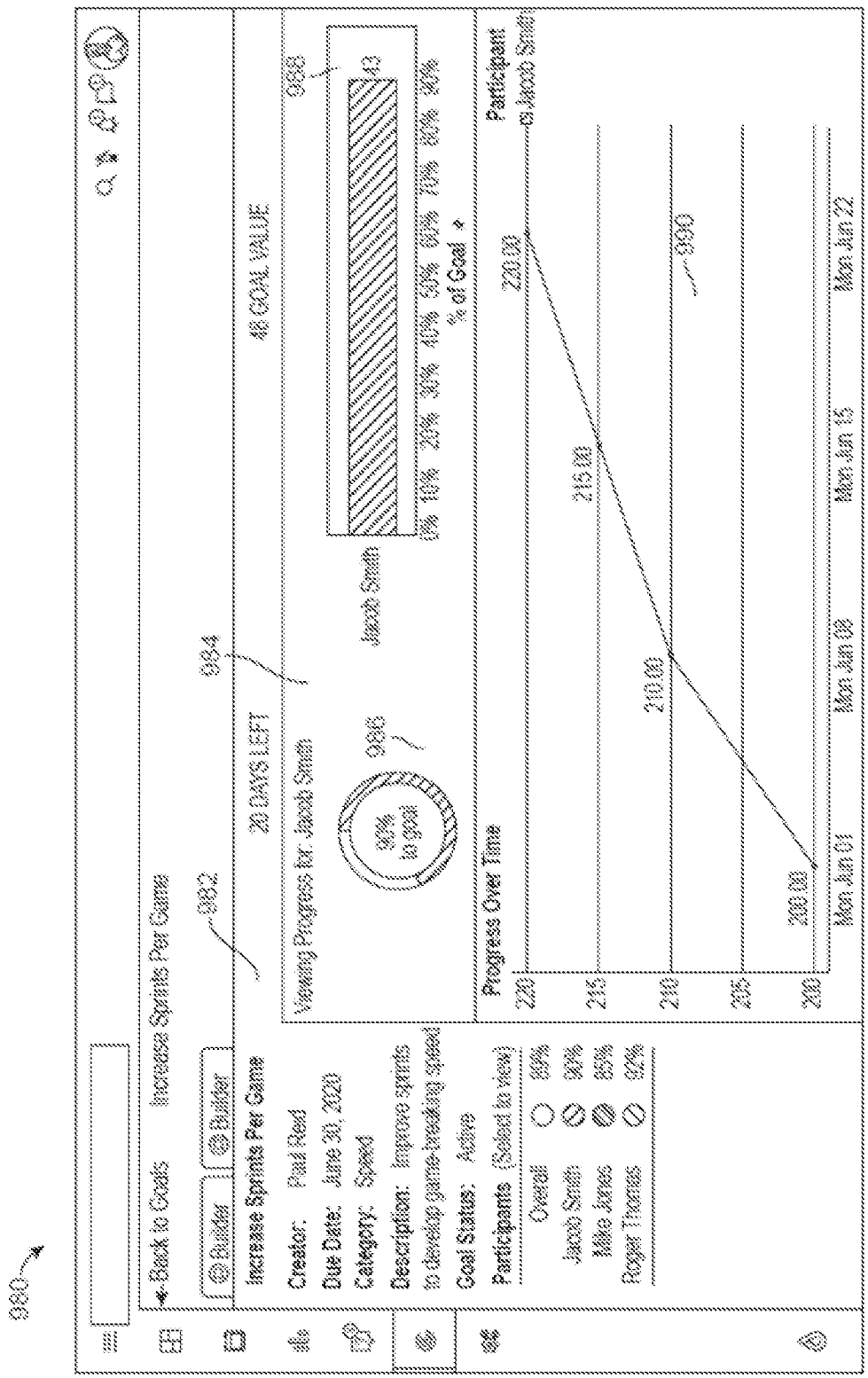
FIG. 9E illustrates another example user interface for displaying progress information to some embodiments.

FIG. 9E illustrates another example user interface 980 for displaying progress information to some embodiments. The user interface 980 displays progress information for a goal 982 for a particular individual, Jacob Smith 984. The progress information includes visual representations of progress percentage 986 and 988, as well as a graph 990 of progress over time for Jacob Smith 984.

FIGS. 10A and 10B illustrate example user interfaces 1000 and 1050 illustrating training plan progress, according to some embodiments. The user interfaces 1000 and 1050 may be displayed to a particular individual in an organization to perform functions such as viewing progress, completing trainings, and entering information. In this example, the user interfaces 1000 and 1050 are displayed in a mobile application on a mobile device.

Referring to FIG. 10A, the interface 1000 displays a training plan 1002 overview. The name of the training plan 1002 is displayed—"How to interact effectively within a competitive environment." The training plan progress 1004 is displayed as a visual representation of the individual's progress towards completing the training plan. The interface 1000 further lists a set of trainings 1006 that make up the training plan—"how to communicate assertively," "develop effective interpersonal skills," and "active listening." The interface 1000 may, responsive to detecting user interaction with a particular training 1006 (e.g., with a touchscreen of the mobile device), transition to a view such as that shown in user interface 1050 of FIG. 10B to drill down into a particular selected training 1006.

As shown in FIG. 10B, the user interface 1050 is a modified view of the training view of user interface 1000. Like the user interface 1000, user interface 1050 shows a training 1002 and an indication of progress towards completion of that training 1004. The user interface 1050 shows a modified training view 1108 drilling down into a particular training, "How to communicate assertively." The training view 1108 shows a set of tasks for completion of the "How to communicate assertively" training: effective communication in the workplace, overcoming challenging situations, making an authentic connection, mastering assertiveness, and a quiz. Check marks are shown indicating which tasks have been completed.

In some aspects, a user can interact with each task to navigate to another interface view for completing the task (e.g., a GUI for completing a quiz, test, or training). In some aspects, these training plans, quizzes, etc. can be configured by an administrator using interfaces similar to those shown in FIGS. 9A-9B.

The techniques described herein provide several advantages. The system utilizes specialized wearable devices to retrieve time-series data for an individual, which is analyzed by the system to predict an adverse physical effect and display a warning and/or modify a schedule to avoid the adverse effect. This can help avoid injuries and improve the functioning of an organization overall. Furthermore, using the skills matrix and user configurable interfaces described herein, the look and feel of the user interfaces can be improved to clearly identify and display a set of goals to a user in a streamlined fashion.

It should be appreciated that the system for predicting an adverse physical effect may have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless of how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A computer-implemented method of forecasting and preventing a non-contact injury of an athlete, the method comprising:
   receiving, by a server computer from one or more wearable devices worn by the athlete comprising a heart rate monitor, an oximetry sensor, and a Global Positioning System (GPS), an average heartrate, an average blood oxygenation, and a distance traveled of the athlete for an athletic session;
   causing display, by the server computer on a graphical user interface displayed on a user device, of interface elements for receiving user input;
   receiving, by the server computer from the user device via the interface elements, a recorded subjective perception from the athlete of the athlete's physical exertion for the athletic session, the subjective perception recorded after the athletic session;
   multiplying, by the server computer, the average heartrate, the average blood oxygenation, and the distance traveled by the subjective perception in order to produce a plurality of work load values for the session;
   computing, by the server computer, a ratio of a work load value, of the plurality of work load values for the session, to an average of workloads over multiple weeks of sessions;
   transmitting, by the server computer, a warning that is triggered based on the ratio breaching a threshold value, the warning indicating a predicted adverse physical effect, wherein transmitting the warning comprises causing the graphical user interface on the user device to be updated to display the warning;
   based on the ratio breaching the threshold value, identifying, by the server computer, a training session to remove from a schedule of the athlete to avoid the adverse physical effect, wherein identifying the training session comprises:
      searching, by the server computer, a training matrix based on a role of the athlete, wherein the training matrix comprises an organized set of rules for managing skill goals within an organization,
      accessing, by the server computer, a calendar of the athlete via an Application Programming Interface (API), and
      comparing, by the server computer, at least one training session in the calendar to recommendations in the training matrix;
   automatically modifying, by the server computer, the calendar of the athlete to delete the identified training session from the calendar; and
   causing, by the server computer, display of the modified calendar on the graphical user interface.

2. The method of claim 1, wherein transmitting the warning includes sending a first electronic mail (email) message.

3. The method of claim 2, the method further comprising:
   including in the first email message the average heartrate, the average blood oxygenation, or the distance traveled, the first email being sent to the athlete; and
   preparing a second email message, the second email message identifying the athlete but omitting the average heartrate, the average blood oxygenation, or the distance traveled, the second email being sent to a coach of the athlete.

4. The method of claim 1, wherein the threshold value for the ratio is 1.5.

5. The method of claim 1, further comprising:
   receiving timestamped heartrate data or timestamped blood oxygenation data; and
   averaging the timestamped heartrate data or timestamped blood oxygenation data in order to calculate the average heartrate or the average blood oxygenation.

6. A system for forecasting and preventing a non-contact injury of an athlete, comprising:
   one or more processors; and
   one or more non-transitory computer-readable media comprising code, executable by the one or more processors, for implementing operations comprising:
   receiving, by a server computer from one or more wearable devices worn by the athlete comprising a heart rate monitor, an oximetry sensor, and a Global Positioning System (GPS), an average heartrate, an average blood oxygenation, and a distance traveled of the athlete for an athletic session;
   causing display, by the server computer on a graphical user interface displayed on a user device, of interface elements for receiving user input;
   receiving, by the server computer from the user device via the interface elements, a recorded subjective perception from the athlete of the athlete's physical exertion for the athletic session, the subjective perception recorded after the athletic session;
   multiplying, by the server computer, the average heartrate, the average blood oxygenation, and the distance traveled by the subjective perception in order to produce a plurality of work load values for the session;
   computing, by the server computer, a ratio of a work load value, of the plurality of work load values for the session, to an average of workloads over multiple weeks of sessions;
   transmitting, by the server computer, a warning that is triggered based on the ratio breaching a threshold value, the warning indicating a predicted adverse physical effect, wherein transmitting the warning comprises causing the graphical user interface on the user device to be updated to display the warning;
   based on the ratio breaching the threshold value, identifying, by the server computer, a training session to remove from a schedule of the athlete to avoid the adverse physical effect wherein identifying the training session comprises:
      searching, by the server computer, a training matrix based on a role of the athlete, wherein the training matrix comprises an organized set of rules for managing skill goals within an organization,
      accessing, by the server computer, a calendar of the athlete via an Application Programming Interface (API), and comparing, by the server computer, at least one training session in the calendar to recommendations in the training matrix;

automatically modifying, by the server computer, the calendar of the athlete to delete the identified training session from the calendar; and causing, by the server computer, display of the modified calendar on the graphical user interface.

7. The system of claim 6, wherein transmitting the warning includes sending a first electronic mail (email) message.

8. The system of claim 7, the operations further comprising:

including in the first email message the average heartrate, the average blood oxygenation, or the distance traveled, the first email being sent to the athlete; and preparing a second email message, the second email message identifying the athlete but omitting the average heartrate, the average blood oxygenation, or the distance traveled, the second email being sent to a coach of the athlete.

9. The system of claim 6, wherein the threshold value for the ratio is 1.5.

10. The system of claim 6, the operations further comprising:

receiving timestamped heartrate data or timestamped blood oxygenation data; and averaging the timestamped heartrate data or timestamped blood oxygenation data in order to calculate the average heartrate or the average blood oxygenation.

* * * * *